US010898217B2

(12) United States Patent
Locke et al.

(10) Patent No.: US 10,898,217 B2
(45) Date of Patent: Jan. 26, 2021

(54) DRESSING PROVIDING APERTURES WITH MULTIPLE ORIFICE SIZES FOR NEGATIVE-PRESSURE THERAPY

(71) Applicant: KCI Licensing, Inc., San Antonio, TX (US)

(72) Inventors: Christopher Brian Locke, Bournemouth (GB); Timothy Mark Robinson, Shillingstone (GB); Diwi L. Allen, San Antonio, TX (US); Prathamesh Kharkar, San Antonio, TX (US); Marisa Schmidt, San Antonio, TX (US); Justin Rice, San Antonio, TX (US); Shannon C. Ingram, Bulverde, TX (US); Kenneth R. Smith, San Antonio, TX (US); Benjamin Andrew Pratt, Poole (GB); Christopher A. Carroll, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 198 days.

(21) Appl. No.: 15/960,310

(22) Filed: Apr. 23, 2018

(65) Prior Publication Data

US 2018/0235646 A1 Aug. 23, 2018

Related U.S. Application Data

(60) Continuation of application No. 15/884,149, filed on Jan. 30, 2018, now Pat. No. 10,743,900, which is a (Continued)

(51) Int. Cl.
*A61B 17/32* (2006.01)
*A61M 1/00* (2006.01)
(Continued)

(52) U.S. Cl.
CPC ........ *A61B 17/32* (2013.01); *A61B 17/22004* (2013.01); *A61F 13/00068* (2013.01);
(Continued)

(58) Field of Classification Search
CPC .............. A61B 17/32; A61B 17/22004; A61B 2017/00761; A61F 13/00042;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for corresponding Application No. PCT/US2019/027463, dated Jul. 4, 2019.
(Continued)

*Primary Examiner* — Katrina M Stransky

(57) ABSTRACT

In one example embodiment, an apparatus for treating a tissue site may include a contact layer formed from a compressible material. The contact layer may include a plurality of apertures extending at least partially through the contact layer. The contact layer may be configurable such that at least a portion of the apertures include a first plurality of orifices having a diameter in a first diameter range and such that at least a portion of the apertures include a second plurality of orifices having a diameter in a second diameter range. The first diameter range may be from about 2 mm to about 6 mm. The second diameter range may be from about 8 mm to about 15 mm. The apparatus may include a cover
(Continued)

configured to form a sealed space including the contact layer and the tissue site.

79 Claims, 22 Drawing Sheets

Related U.S. Application Data division of application No. 14/708,109, filed on May 8, 2015, now Pat. No. 9,918,733.

(60) Provisional application No. 61/991,134, filed on May 9, 2014, provisional application No. 61/991,174, filed on May 9, 2014, provisional application No. 61/991,150, filed on May 9, 2014.

(51) Int. Cl.
| | |
|---|---|
| *A61B 17/22* | (2006.01) |
| *A61F 13/00* | (2006.01) |
| *A61F 13/02* | (2006.01) |
| *A61M 27/00* | (2006.01) |
| *A61B 17/00* | (2006.01) |

(52) U.S. Cl.
CPC ....... *A61F 13/0216* (2013.01); *A61M 1/0084* (2013.01); *A61M 1/0088* (2013.01); *A61B 2017/00761* (2013.01); *A61B 2017/22008* (2013.01); *A61B 2017/22089* (2013.01); *A61B 2017/32006* (2013.01); *A61B 2017/320008* (2013.01); *A61B 2017/320064* (2013.01); *A61F 2013/00251* (2013.01); *A61M 1/0025* (2014.02); *A61M 27/00* (2013.01); *A61M 2205/3344* (2013.01)

(58) Field of Classification Search
CPC ............ A61F 13/00068; A61F 13/0216; A61F 2013/00255; A61F 13/00029; A61F 2013/00251; A61M 1/0084; A61M 1/0088; A61M 1/009; A61M 1/0025; A61M 27/00

See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 3,449,509 A1 | 5/2013 | Weston |
| 8,529,548 B2 | 9/2013 | Blott et al. |

(56) References Cited

U.S. PATENT DOCUMENTS

| | | | |
|---|---|---|---|
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 9,974,694 | B2 | 5/2018 | Locke et al. |
| 2001/0037118 | A1 | 11/2001 | Shadduck |
| 2002/0065494 | A1 | 5/2002 | Lockwood et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0161346 | A1* | 10/2002 | Lockwood .......... A61M 1/0058 604/315 |
| 2008/0177253 | A1 | 7/2008 | Boehringer et al. |
| 2008/0275409 | A1* | 11/2008 | Kane ................ A61F 13/00068 604/305 |
| 2009/0093779 | A1 | 4/2009 | Riesinger |
| 2010/0063484 | A1 | 3/2010 | Heagle |
| 2010/0160871 | A1 | 6/2010 | Seegert et al. |
| 2010/0160874 | A1 | 6/2010 | Robinson et al. |
| 2010/0185163 | A1 | 7/2010 | Heagle |
| 2010/0312159 | A1* | 12/2010 | Aali ................. A61F 13/00085 602/44 |
| 2011/0178451 | A1 | 7/2011 | Robinson et al. |
| 2011/0213319 | A1 | 9/2011 | Blott et al. |
| 2011/0230809 | A1 | 9/2011 | Manwaring et al. |
| 2012/0143113 | A1 | 6/2012 | Robinson et al. |
| 2012/0143114 | A1 | 6/2012 | Locke et al. |
| 2012/0157945 | A1* | 6/2012 | Robinson ................ A61F 13/02 604/319 |
| 2013/0211349 | A1* | 8/2013 | Stokes ............... A61F 13/00017 604/290 |
| 2013/0274717 | A1 | 10/2013 | Dunn |
| 2014/0066868 | A1 | 3/2014 | Freedman et al. |
| 2014/0163491 | A1 | 6/2014 | Schuessler et al. |
| 2015/0080788 | A1 | 3/2015 | Blott et al. |
| 2015/0201954 | A1 | 7/2015 | Pratt et al. |
| 2017/0189237 | A1 | 7/2017 | Locke et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2008005532 A2 | 1/2008 |
| WO | 2008136998 A1 | 11/2008 |
| WO | 2009021523 A1 | 2/2009 |
| WO | 2010051073 A1 | 5/2010 |
| WO | 2010/075178 A2 | 7/2010 |
| WO | 2013032745 A1 | 3/2013 |
| WO | 2013066426 A2 | 5/2013 |
| WO | 2013071243 A2 | 5/2013 |
| WO | 2013116552 A1 | 8/2013 |
| WO | 2013129343 A1 | 9/2013 |
| WO | 2014/014922 A1 | 1/2014 |
| WO | 2014014871 A1 | 1/2014 |
| WO | 2015172104 A1 | 11/2015 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds

(56) References Cited

OTHER PUBLICATIONS by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 16-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž., Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen", British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for PCT/US2015/030027 dated Jul. 15, 2015.
Partial International Search Report from PCT/US2015/030030 dated Jul. 22, 2015.
International Search Report and Written Opinion for PCT/US2015/030023 dated Aug. 24, 2015.
Extended European Search Report for corresponding Application No. 171862527, dated Nov. 14, 2017.
"Introduction to Polyurethanes: Thermoplastic Polyurethane", American Chemistry Council, https://polyurethane.americanchemistry.com/polyurethanes/Introduction-to-Polyurethanes/Applications/Thermoplastic-Polyurethane/.
Japanese Notice of Rejection for corresponding Application No. 2016-566815, dated Feb. 5, 2019.
Extended European Search Report for corresponding Application No. 18162504.7, dated May 24, 2018.
Japanese Notice of Rejection for corresponding Application No. 2016-566785, dated Jun. 25, 2019.
Japanese Notice of Rejection for corresponding Application No. 2016-566785, dated Jan. 29, 2019.
Japanese Notice of Rejection for Corresponding Application No. 2019-233695, dated Oct. 13, 2020.

* cited by examiner

DRESSING PROVIDING APERTURES WITH MULTIPLE ORIFICE SIZES FOR NEGATIVE-PRESSURE THERAPY

This application is a continuation-in-part of U.S. patent application Ser. No. 15/884,149, entitled "Disruptive Dressing for use with Negative Pressure and Fluid Instillation," by Ingram et al., filed Jan. 30, 2018, which is a divisional of Ser. No. 14/708,109, now U.S. Pat. No. 9,918,733, entitled "Disruptive Dressing for use with Negative Pressure and Fluid Instillation," by Ingram et al., filed May 8, 2014, which claims the benefit, under 35 USC § 119(e), of U.S. Provisional Patent Application Ser. No. 61/991,150, entitled "Subcutaneous Anchor for Surgical Closure," by Locke et al., filed May 9, 2014; U.S. Provisional Patent Application Ser. No. 61/991,174, entitled "Dressing with Contracting Layer for Linear Tissue Sites," by Locke et al., filed May 9, 2014; and U.S. Provisional Patent Application Ser. No. 61/991,134, entitled "Debriding Dressing for use with Negative Pressure and Fluid Instillation," by Locke et al., filed May 9, 2014, all of which are incorporated herein by reference for all purposes.

TECHNICAL FIELD

The invention set forth in the appended claims relates generally to tissue treatment systems and more particularly, but without limitation, to dressings for application to a tissue site, to systems including such dressings, and to methods related to the same.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for systems, dressings, and methods for providing therapy to a tissue site are set forth in the appended claims. Illustrative embodiments are also provided to enable a person skilled in the art to make and use the claimed subject matter.

For example, in some embodiments, an apparatus for treating a tissue site may comprise a contact layer formed from a compressible material. The contact layer may comprise a plurality of apertures extending at least partially through the contact layer. The contact layer may be configurable such that at least a portion of the apertures include a first plurality of orifices having a diameter in a first diameter range and such that at least a portion of the apertures include a second plurality of orifices having a diameter in a second diameter range. The contact layer may also comprise a cover configured to form a sealed space including the contact layer and the tissue site. The first diameter range may be from about 2 mm to about 6 mm. The second diameter range may be from about 8 mm to about 15 mm.

Also for example, an apparatus for treating a tissue site may comprise a contact layer formed from a compressible material. The contact layer may comprise a plurality of apertures extending at least partially through the contact layer. The contact layer may be configurable such that at least a portion of the apertures include a first plurality of orifices having a diameter in a first diameter range and such that at least a portion of the apertures include a second plurality of orifices having a diameter in a second diameter range. The first diameter range may be from about 2 mm to about 6 mm. The second diameter range may be from about 8 mm to about 15 mm. The apparatus may also comprise a cover configured to form a sealed space including the contact layer and the tissue site.

Also for example, an apparatus for treating a tissue site may comprise a contact layer formed from a compressible material. The contact layer may comprise a plurality of removable portions. Each of the plurality of removable portions may have apertures including orifices in a first diameter range. The removable portions may be removable from the contact layer to form apertures including orifices in a second diameter range. The first diameter range may be from about 2 mm to about 6 mm. The second diameter range may be from about 8 mm to about 15 mm. selecting a desired orifice size from either the apertures of the first diameter range or the second diameter range. The apparatus may also comprise a cover configured to form a sealed space including the contact layer and the tissue site.

Also for example, a method for treating a tissue site may comprise providing a contact layer formed from a compressible material and comprising a plurality of apertures extending at least partially through the contact layer. The contact layer may be configurable such that at least a portion of the apertures include a first plurality of orifices having a diameter in a first diameter range and such that at least a portion of the apertures include a second plurality of orifice having a diameter in a second diameter range. The first diameter range may be from about 2 mm to about 6 mm. The second diameter range may be from about 8 mm to about 15 mm. The method may also comprise selecting a desired orifice size from either the apertures of the first diameter range or the second diameter range. The method may also comprise configuring the contact layer such that orifices of the desired orifice size are in contact with the tissue site. The method may also comprise sealing a sealing member to tissue surrounding the tissue site to form a sealed space enclosing the contact layer. The method may also comprise fluidly coupling a negative-pressure source to the sealed space. The method may also comprise supplying reduced pressure to the sealed space and the contact layer to draw tissue through the orifices of the desired orifice size and into the apertures to form nodules.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
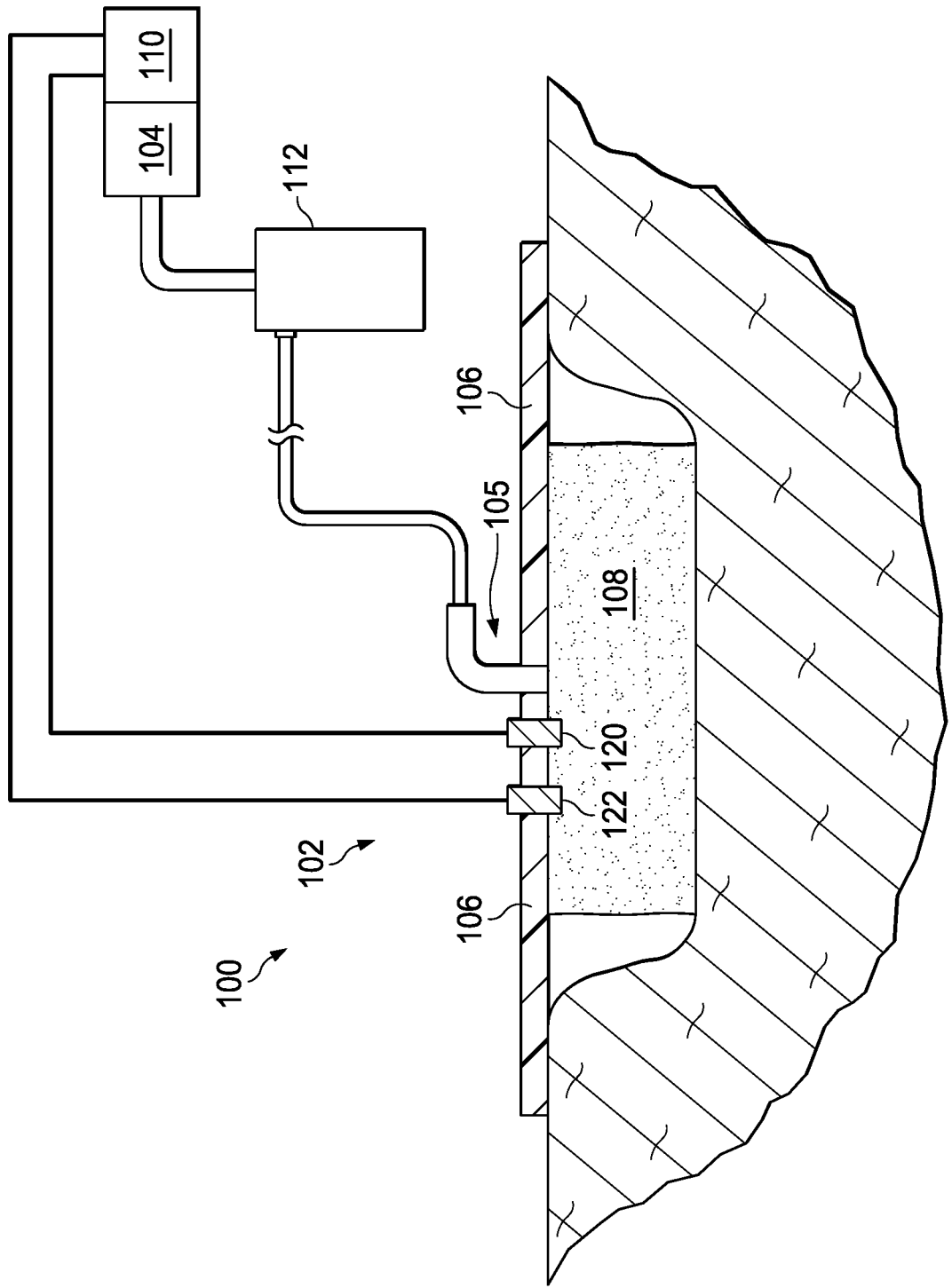
FIG. 1 is a schematic diagram of an example embodiment of a therapy system that can provide negative-pressure therapy in accordance with this specification.

FIG. 1 is a simplified schematic diagram of an example embodiment of a therapy system 100 that can provide negative-pressure therapy in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a contact layer 108. A regulator or a controller, such as a controller 110, may also be coupled to the negative-pressure source 104.

In some embodiments, a dressing interface 105 may facilitate coupling the negative-pressure source 104 to the dressing 102. For example, such a dressing interface may be the SENSAT.R.A.C.™ Dressing available from Acelity L.P. of San Antonio, Tex. The therapy system 100 may optionally include a fluid container, such as a container 112, coupled to the dressing 102 and to the negative-pressure source 104.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of a fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the contact layer 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m$^2$ per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally may be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Contact Layer

The contact layer 108 can be generally adapted to contact a tissue site. The contact layer 108 may be partially or fully in contact with the tissue site. If the tissue site is a wound, for example, the contact layer 108 may partially or completely fill the wound, or may be placed over the wound. The contact layer 108 may take many forms, and may have many sizes, shapes, or thicknesses depending on a variety of factors, such as the type of treatment being implemented or the nature and size of a tissue site. For example, the size and shape of the contact layer 108 may be adapted to the contours of deep and irregular shaped tissue sites. Moreover, any or all of the surfaces of the contact layer 108 may have projections or an uneven, course, or jagged profile that can induce strains and stresses on a tissue site, which can promote granulation at the tissue site.

In some embodiments, the contact layer 108 may comprise or consist of two substantially planar surfaces and a depth or thickness orthogonal to the planar surfaces. For example, the contact layer 108 may comprise a first surface and a second surface. The first surface and/or second surface may have a surface area from about 1 cm$^2$ to about 400 cm$^2$, or from about 2 cm$^2$ to about 200 cm$^2$, or from about 4 cm$^2$ to about 100 cm$^2$.

In some embodiments, the contact layer 108 may comprise or consist of a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site. In some illustrative embodiments, the pathways of a manifold may be interconnected to improve distribution or collection of fluids across a tissue site.

In some embodiments, the contact layer 108 may be formed from a suitably compressible material. For example, in some illustrative embodiments, the contact layer 108 may comprise or consist of a porous foam material having interconnected cells or pores. For example, the contact layer 108 may comprise or consist of cellular foam such as open-cell foam. The open-cell foam may be reticulated foam. Liquids, gels, and other foams may also include or be cured to include fluid pathways. In some embodiments, the contact layer 108 may comprise projections that form interconnected fluid pathways. For example, the contact layer 108 may be molded to provide surface projections that define interconnected fluid pathways. In some embodiments, the foam may have an average pore size that varies according to needs of a prescribed therapy. For example, in some embodiments, the contact layer 108 may be foam having pore sizes in a range of 400-600 microns. In some embodiments, the contact layer 108 may have a tensile strength that also varies according to needs of a prescribed therapy.

In some embodiments, the foam material of the contact layer 108 may be characterized with respect to density. For example, in some embodiments, the contact layer 108 may be characterized as a relatively dense material. In various embodiments, the contact layer 108 may have a density of about 24 kg/m$^3$ to about 125 kg/m$^3$ or about 24 kg/m$^3$ to about 72 kg/m$^3$.

In some embodiments, the contact layer 108 may comprise a single foam layer. In some embodiments, the contact layer 108 may comprise two or more layers that have been joined together to form the contact layer 108. The two or more sublayers may be joined together by flame lamination or by a reactive adhesive, for example, a heat reactive adhesive system such as a hot melt adhesive or a chemically reactive adhesive system such as isocyanate adhesives, epoxy adhesives, silane adhesives, or combinations thereof.

In some embodiments, the contact layer 108 may be hydrophobic. In some an embodiments, the hydrophobic characteristics may prevent the foam from directly absorbing fluid, such as wound exudate, but may allow fluid to pass through a fluid pathway. For example, in some embodiments, the foam may be polyurethane foam, a silicone foam, a polyether block amide foam, such as PEBAX®, an acrylic foam, a polyvinyl chloride (PVC) foam, a polyolefin foam, a polyester foam, a polyamide foam, a thermoplastic elastomer (TPE) foam such as a thermoplastic vulcanizate (TPV) foam, or another crosslinking elastomeric foam such as foams formed from styrene-butadiene rubber (SBR) and ethylene propylene diene monomer (EPDM) rubber. For example, the contact layer 108 may comprise hydrophobic, open-cell foam. In one non-limiting example, the contact layer 108 may comprise a reticulated polyurethane foam such as the foam employed in the V.A.C.® GRANUFOAM™ Dressing or the foam employed in the V.A.C. VERAFLO™ Dressing, both available from Acelity L.P., Inc. of San Antonio, Tex.

In other embodiments, the contact layer 108 may be hydrophilic. In some embodiments, the hydrophillic characteristics may be effective to wick fluid while also continuing to distribute negative pressure to the tissue site. In some embodiments, the wicking properties of the contact layer 108 may draw fluid away from the tissue site by capillary flow or other wicking mechanisms. An example of a hydrophilic foam may include a polyvinyl alcohol or polyether, open-cell foam. Other foams that may exhibit hydrophilic characteristics include hydrophobic foams that have been treated or coated to provide hydrophilicity. For example, the contact layer 108 may be a treated open-cell polyurethane foam. In one non-limiting example, the contact layer 108 may comprise a polyvinyl alcohol, open-cell foam such as the foam employed in the V.A.C. WHITEFOAM™ Dressing available from Acelity L.P., Inc. of San Antonio, Tex.

In some embodiments, the contact layer 108 may further promote granulation at a tissue site when pressure within a sealed therapeutic environment is reduced. For example, any or all of the surfaces of the contact layer 108 may have an uneven, coarse, or jagged profile that can induce microstrains and stresses at a tissue site if negative pressure is applied through contact layer 108.

In some embodiments, the contact layer 108 may comprise a plurality of apertures extending at least partially through the thickness of the contact layer 108. The contact layer 108 may be configurable such that at least a portion of the apertures include a first plurality of orifices having a diameter in a first diameter range, and such that at least a portion of the apertures include a second plurality of orifices having a diameter in a second diameter range. The term "aperture" in this context broadly refers to a void space extending some depth into or through a contact layer. The term "orifice" in this context more narrowly refers to an opening to an aperture in a plane in which an aperture intersects either the first surface or the second surface of the contact layer 108.

In some embodiments, the first diameter range may be from about 2 mm to about 6 mm, or from about 3 mm to about 5 mm. The second diameter range may be from about 8 mm to about 15 mm, or from about 10 mm to about 15, or from about 8 mm to about 12 mm, or from about 10 mm to about 12. Suitable sizes for the first orifice and the second orifice may be determined based upon the particular needs of a prescribed therapy.

Figure 2:
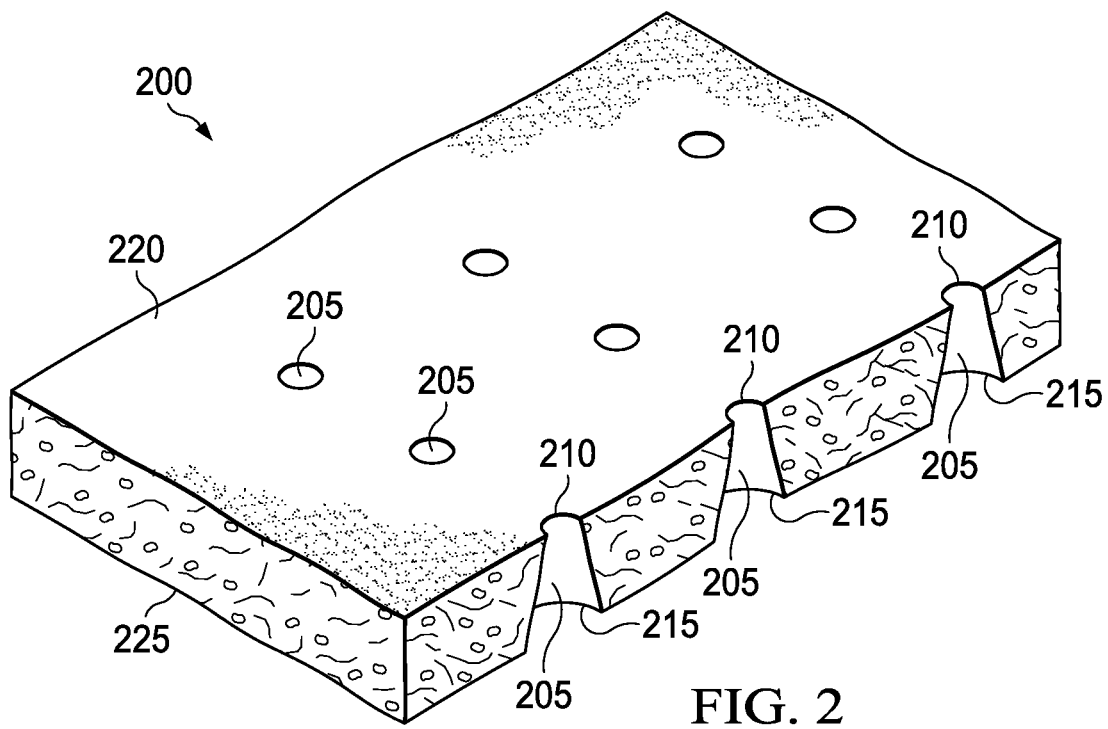
FIG. 2 is a simplified cutaway view of an example embodiment of a contact layer that may be associated with the therapy system of FIG. 1.

In some embodiments, a contact layer may comprise a plurality of apertures extending through the contact layer, each having an orifice within the first diameter range and an orifice within the second diameter range. For example, FIG. 2 is a simplified cutaway view of an example embodiment of a contact layer 200 including a plurality of apertures 205 extending through the contact layer 200. The apertures 205 may each have a first orifice 210 having a diameter in the first diameter range and a second orifice 215 having a diameter in the second diameter range. The apertures 205 may have a suitable transitional shape between the first orifice 210 and the second orifice 215. For example, in the embodiment FIG. 2, the apertures 205 have a variable diameter, and may define a conical frustum void-space. In some embodiments, the first orifices 210 may be disposed on a first surface 220 of the contact layer 200 and the second orifices 215 may be disposed on a second surface 225 of the contact layer 200.

Figure 3:
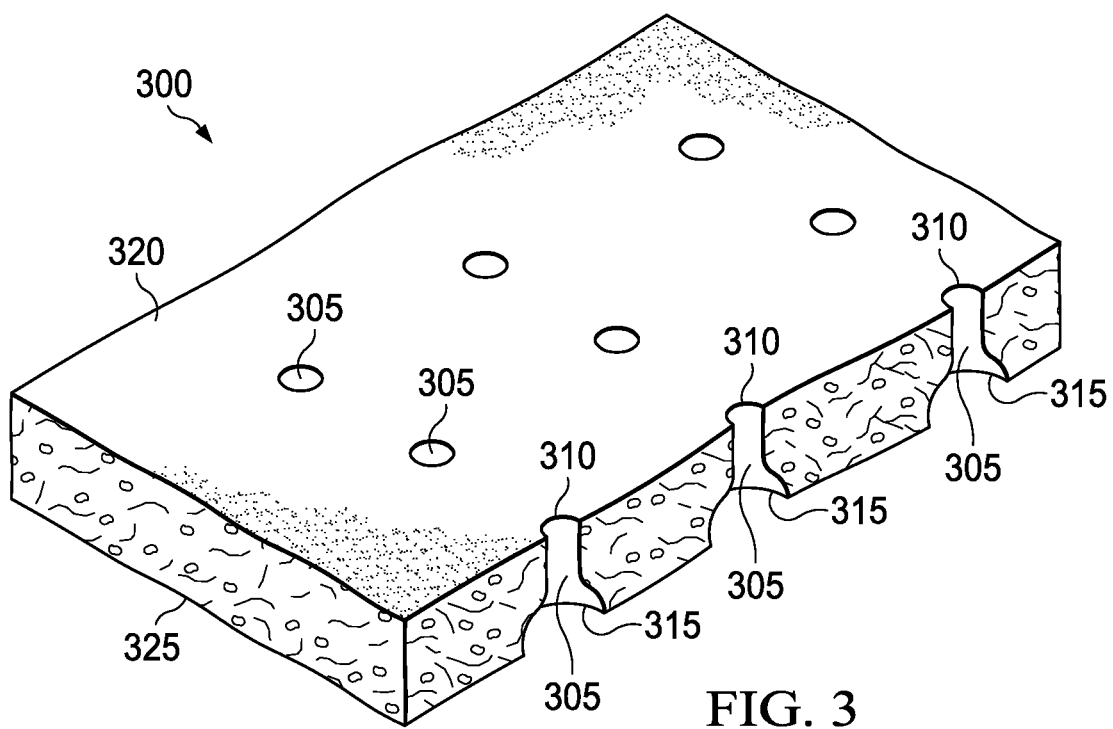
FIG. 3 is a simplified cutaway view of another example embodiment of a contact layer that may be associated with the therapy system of FIG. 1.

FIG. 3 is a simplified cutaway view of another example embodiment of a contact layer 300 including a plurality of apertures 305 extending through the contact layer 300 and having a first orifice 310 having a diameter in the first diameter range and a second orifice 315 having a diameter in the second diameter range. In the embodiment of FIG. 3, the aperture 305 may define at least a portion of a hyper- boloidic void-space, for example a "bottle-shaped" void-space. The first orifices 310 may be disposed on a first surface 320 of the contact layer 300 and the second orifices 315 may be disposed on a second surface 325 of the contact layer 300.

Figure 4:
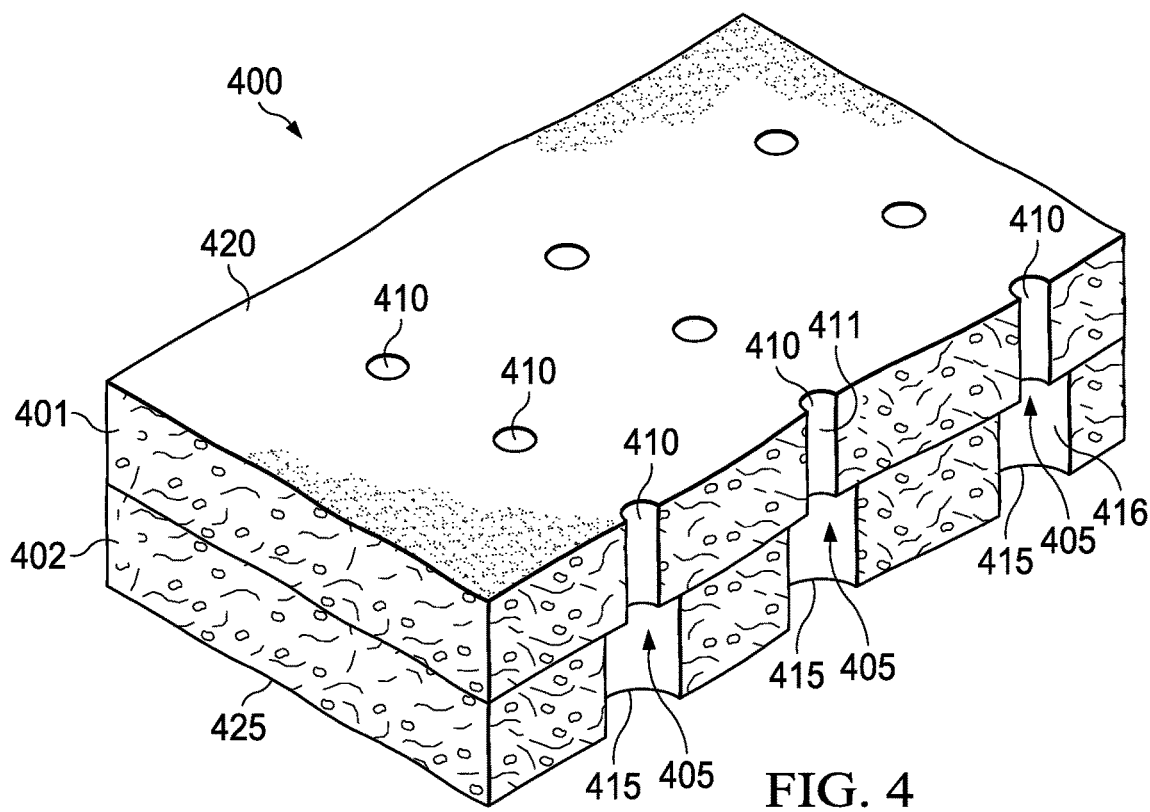
FIG. 4 is a simplified cutaway view of another example embodiment of a contact layer that may be associated with the therapy system of FIG. 1.

FIG. 4 is a simplified cutaway view of another example embodiment of a contact layer 400 including a plurality of apertures 405 extending through the contact layer 400 and having a first orifice 410 having a diameter in the first diameter range and a second orifice 415 having a diameter in the second diameter range. The contact layer 400 may comprise a first sublayer 401 joined to a second sublayer 402. In the embodiment FIG. 4, the apertures 405 include a first portion 411 extending through the first sublayer 401 and a second portion 416 extending through the second sublayer 402. As shown in the example of FIG. 4, the first portion 411 may be narrower than the second portion 416. The first orifices 410 may be disposed on a first surface 420 of the contact layer 400 and the second orifices 415 may be disposed on a second surface 425 of the contact layer 400.

Figure 5:
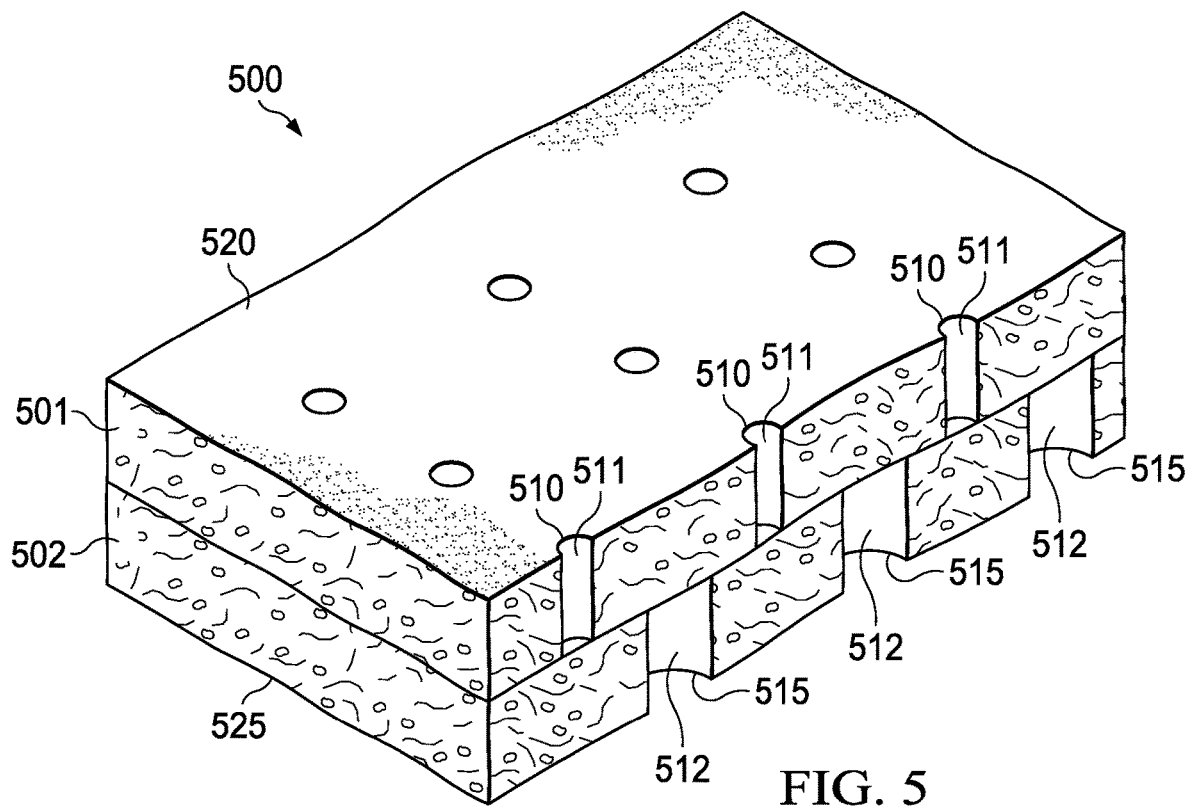
FIG. 5 is a simplified cutaway view of another example embodiment of a contact layer that may be associated with the therapy system of FIG. 1.

In some embodiments, a contact layer may comprise a plurality of apertures extending only partially through the contact layer. A first portion of the apertures may extend from a first surface and have orifices within the first diameter range. A second portion of the apertures may extend from a second surface and have orifices within the second diameter range. FIG. 5 is a simplified cutaway view of another example embodiment of a contact layer 500 comprising a first sublayer 501 joined to a second sublayer 502. A first plurality of apertures 511 having orifices within the first diameter range may extend through the first sublayer 501. A second plurality of apertures 512 having orifices within the second diameter range may extend through the second sublayer 502. The first plurality of apertures 511 may be offset with respect to the second plurality of apertures 512, for example, such that the first plurality of apertures 511 and the second plurality of apertures 512 each extend only partially through the contact layer 500. The first orifices 510 may be disposed on a first surface 520 of the contact layer 500 and the second orifices 515 may be disposed on a second surface 525 of the contact layer 500.

Figure 6:
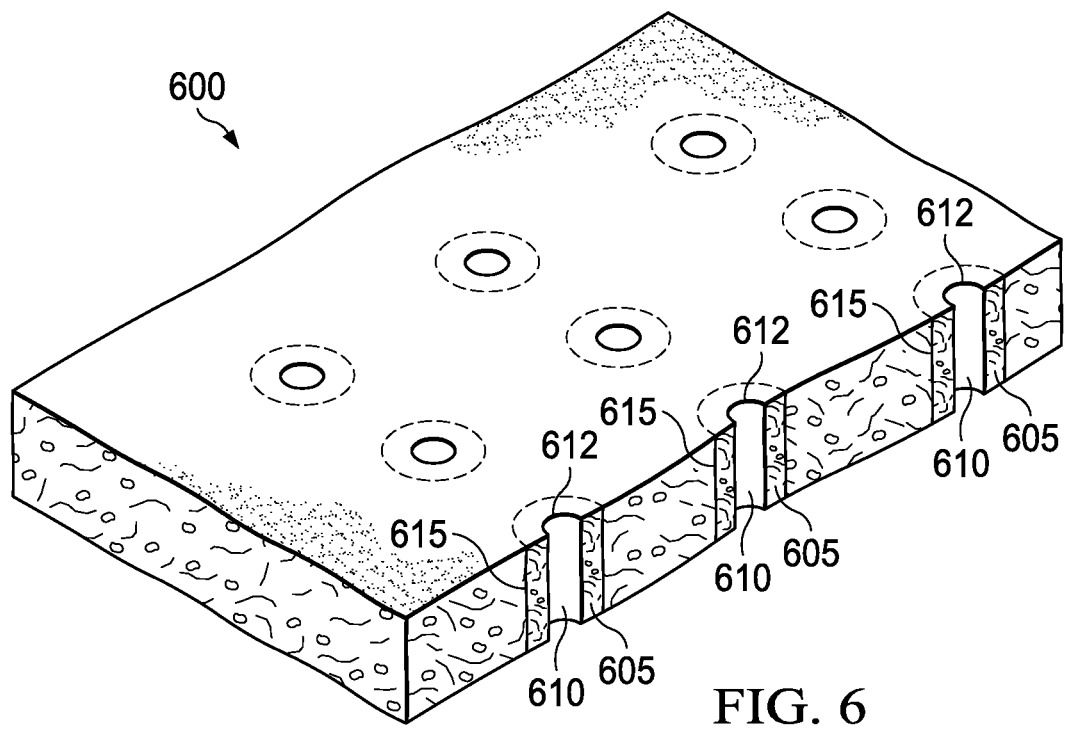
FIG. 6 is a simplified cutaway view of another example embodiment of a contact layer that may be associated with the therapy system of FIG. 1.

In some embodiments, a contact layer may comprise a plurality of removable portions. The plurality of removable portions may have apertures including orifices in a first diameter range. The removable portions may be removable from the contact layer to form apertures including orifices in a second diameter range. FIG. 6 is a simplified cutaway view of another example embodiment of a contact layer 600. The contact layer 600 may comprise a plurality of removable portions 605. Each of the removable portions may include a first aperture 610 having first orifices 612 in the first diameter range. Each of the removable portions 605 may be fitted within a second aperture 615 of the contact layer 600. In some embodiments, the removable portions 605 may comprise a material separate from the contact layer 600 that is inserted within the second apertures 615 and held in place, for example, by friction. In some, other embodiments, the removable portions 605 may be formed from the material that also forms the contact layer 600. For example, in such embodiments, the removable portions 605 may be formed by cutting or perforating the contact layer 600 and leaving the removable portions 605 in place.

Figure 7:
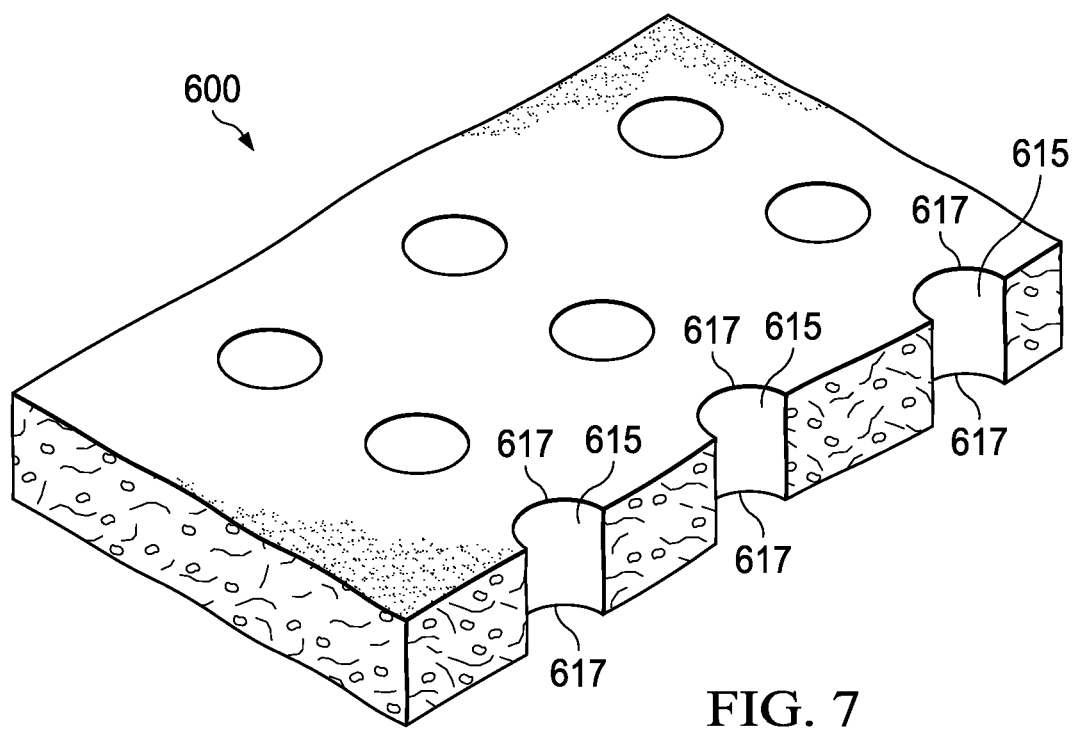
FIG. 7 is another simplified cutaway view of the example embodiment of the contact layer of FIG. 6.

FIG. 7 is another simplified cutaway view of the embodiment of the contact layer 600 of FIG. 6, illustrating the removable portions 605 removed. In some embodiments, each of the removable portions 605 may be removable to yield the second apertures 615 having second orifices 617 in the second diameter range. In some embodiments, the first apertures 610, the second apertures 615, or both may have a substantially constant diameter. For example, each of the first apertures 610 may include two first orifices 612 in the first diameter range and each of the second apertures 615 may include two second orifices 617 in the second diameter range.

In some, other embodiments, the first apertures 610, the second apertures 615, or both may have a diameter that varies over the thickness of the contact layer 600. For example, each of the first apertures 610 may include two orifices having different diameters, each of the second apertures 615 may include two orifices having different diameters. For example, the first apertures 610, the second apertures 615, or both may define at least a portion of a conical void-space, a hyperboloidic void-space, or the like. In such embodiments, the contact layer may be configurable to provide orifices having diameters within a first diameter range, orifices having diameters within a second diameter range, orifices having diameters within a third diameter range, and orifices having diameters within a fourth diameter range.

Figure 8:
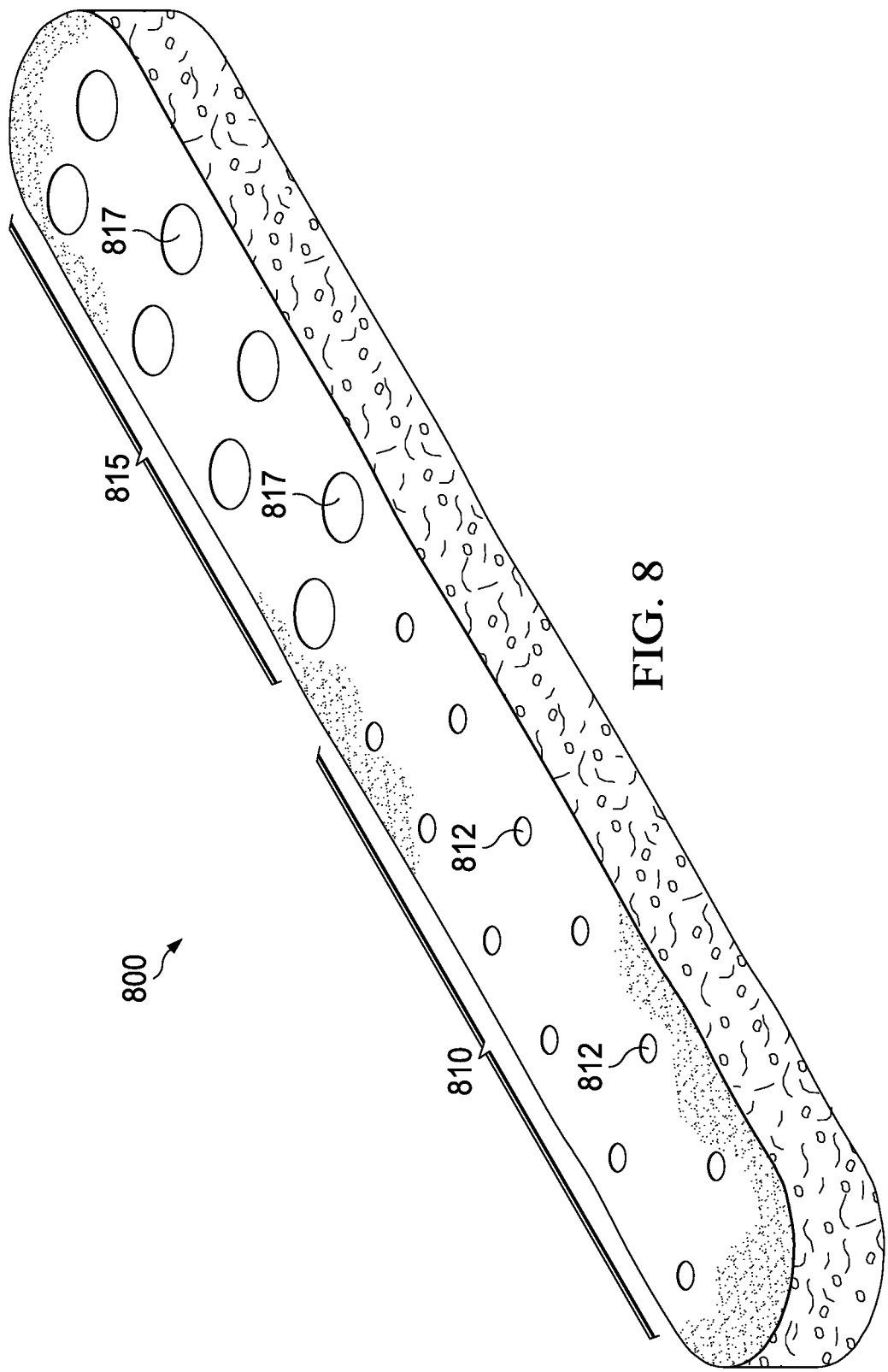
FIG. 8 is a simplified perspective view of an example embodiment of a contact layer that may be associated with the therapy system of FIG. 1.
Figure 9:
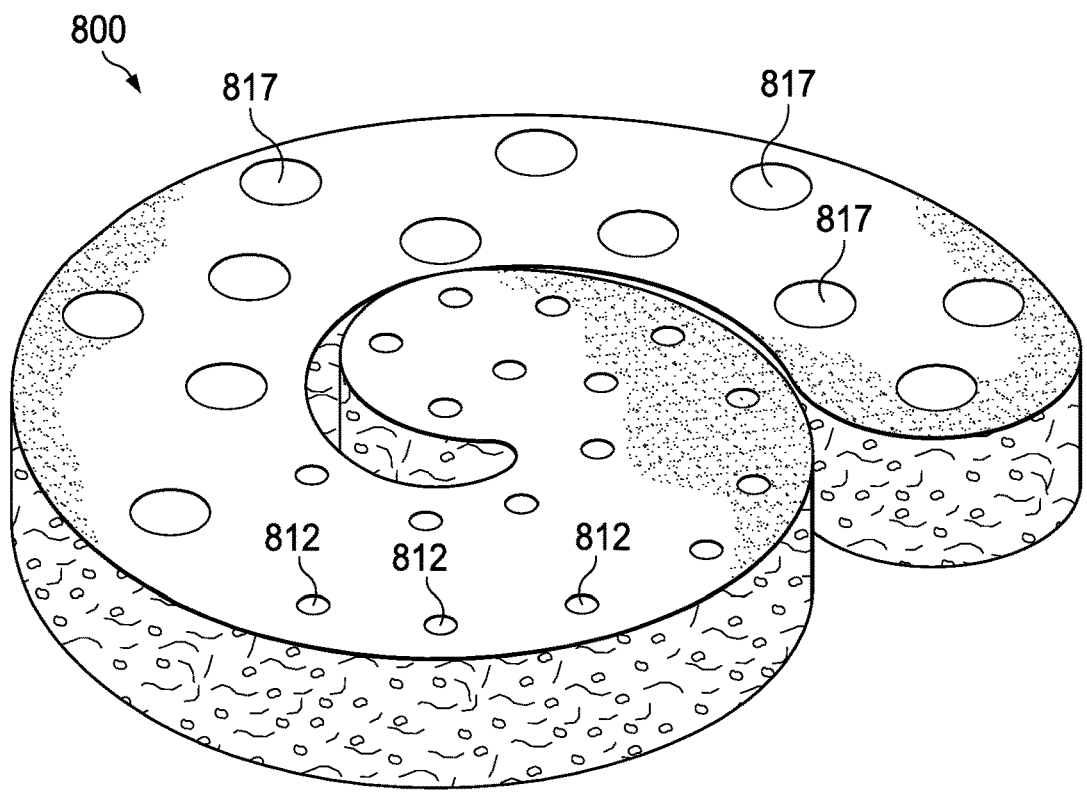
FIG. 9 is another simplified perspective view of the example embodiment of the contact layer of FIG. 8.
Figure 10:
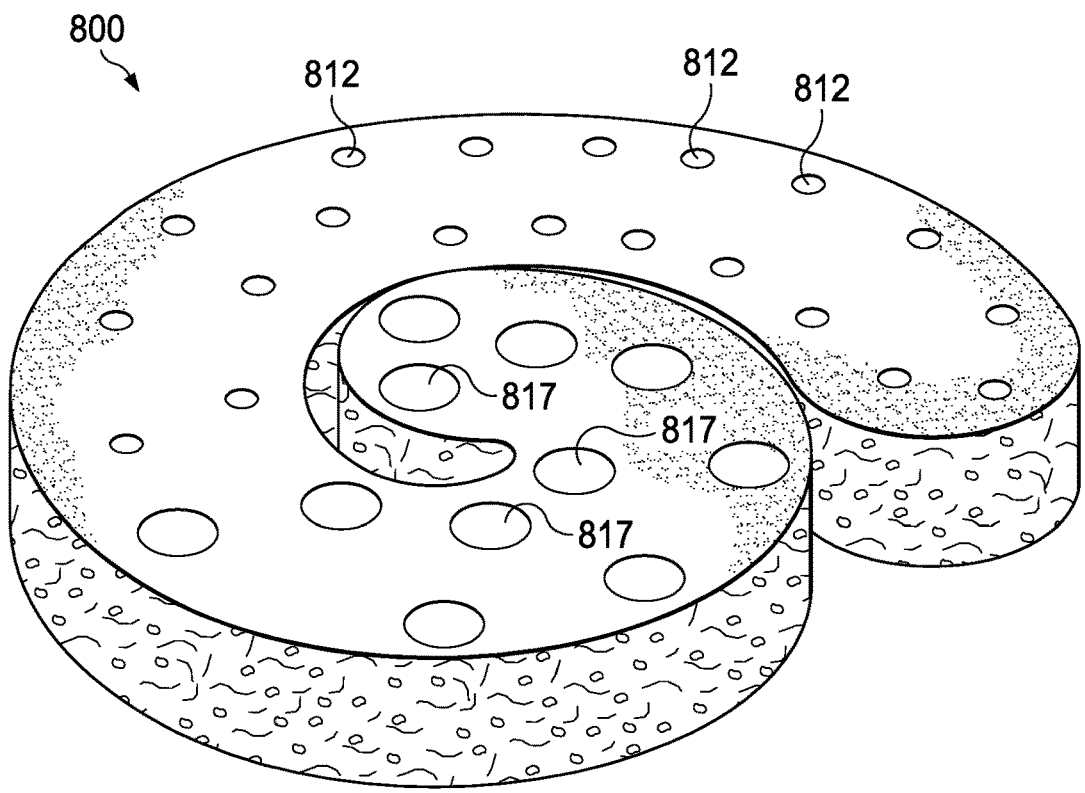
FIG. 10 is another simplified perspective view of the example embodiment of the contact layer of FIG. 8.

In some embodiments, a contact layer may comprise a first plurality of apertures including orifices having diameters within a first diameter range and a second plurality of apertures including orifices having diameters within a second diameter range. FIG. 8 is a simplified perspective view of another example embodiment of a contact layer 800. The contact layer 800 may include a first plurality of apertures 810 and a second plurality of apertures 815. The first plurality of apertures 810 and the second plurality of apertures 815 may extend partially or entirely through the contact layer 800. Each of the first plurality of apertures 810 may include an orifice 812 having a diameter within a first diameter range and each of the second plurality of apertures 815 may include an orifice 817 having a diameter within a second diameter range. In some embodiments, the first plurality of apertures 810 may be grouped together and the second plurality of apertures 815 may also be grouped together. For example, the first plurality of apertures 810 may be generally disposed in a first portion of the contact layer 800 and the second plurality of apertures 815 may be generally disposed in a second portion of the contact layer 800. The contact layer 800 may be configurable in either a first configuration or a second configuration, for example, such that either the orifices 812 having a diameter within a first diameter range or the orifices 817 having a diameter within a second diameter range are disposed centrally with respect to the contact layer. For example, FIG. 9 illustrates the contact layer 800 of FIG. 8 in a first conformation in which the contact layer 800 is coiled such that the orifices 812 having a diameter within a first diameter range are disposed centrally after the contact layer 800 has been formed into a spiral. In some embodiments, the contact layer may be provided in such a spiral conformation. Also for example, FIG. 10 illustrates the contact layer 800 of FIG. 8 in a second conformation in which the contact layer 800 is coiled such that the orifices 817 having a diameter within a second diameter range are disposed centrally after the contact layer 800 has been formed into a spiral.

In various embodiments, the first surface and/or the second surface of the contact layer 108 may have any suitable shape, examples of which include but are not limited to, triangles, squares, rectangles, ellipses, circles, ovals, and various polygons having four, five, six, seven, eight, or more sides. The shape and area of the first surface and the second surface may be customized to the location and type of tissue site onto which the contact layer 108 is to be applied. In some embodiments, the contact layer 108 may have a thickness from about 10 mm to about 500 mm, for example, from about 10 mm to about 100, or from about 100 mm to about 200 mm, or from about 200 mm to about 300 mm, or from about 300 mm to about 400 mm, or from about 400 mm to about 500 mm.

In some embodiments, the contact layer 108 may be configurable into a one of multiple, potential sizes or shapes, as desired. For example, in some embodiments, the contact layer 108 may comprise one or more separation-lines, such as perforations, slits, splits, indentions, or the like. For example, the separation-lines may enable the contact layer 108 to be conformed to a tissue site having a particular size or shape by a user without the use of additional tools. For example, the separation-lines may enable to user to divide the contact layer 108 into various portions. In various embodiments, the separation-lines may be disposed within the contact layer 108 in any suitable pattern or combination of patterns such that, when separated along the separation-lines, one or more of the resultant portions of the contact layer 108 have a desired size and/or shape. The perforations may allow a contact layer 108 to be customized to one of multiple sizes or shapes. The contact layer 108 may offer multiple combinations of lines along which the contact layer 108 can be separated, for example, such that multiples potential size and shape combinations are possible.

Figure 11:
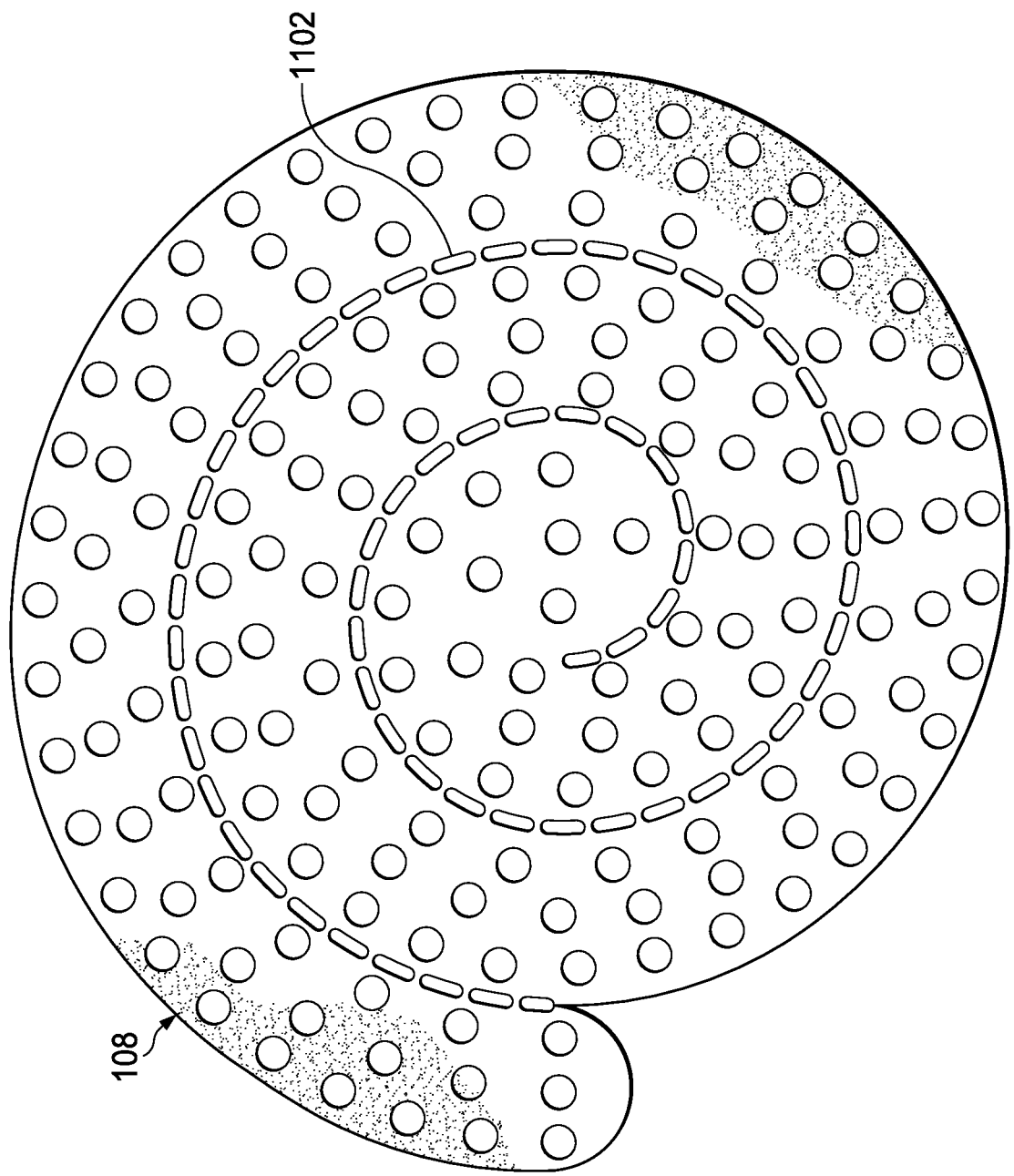
FIG. 11 is a simplified planar view of another example embodiment of a contact layer that may be associated with the therapy system of FIG. 1.
Figure 12:
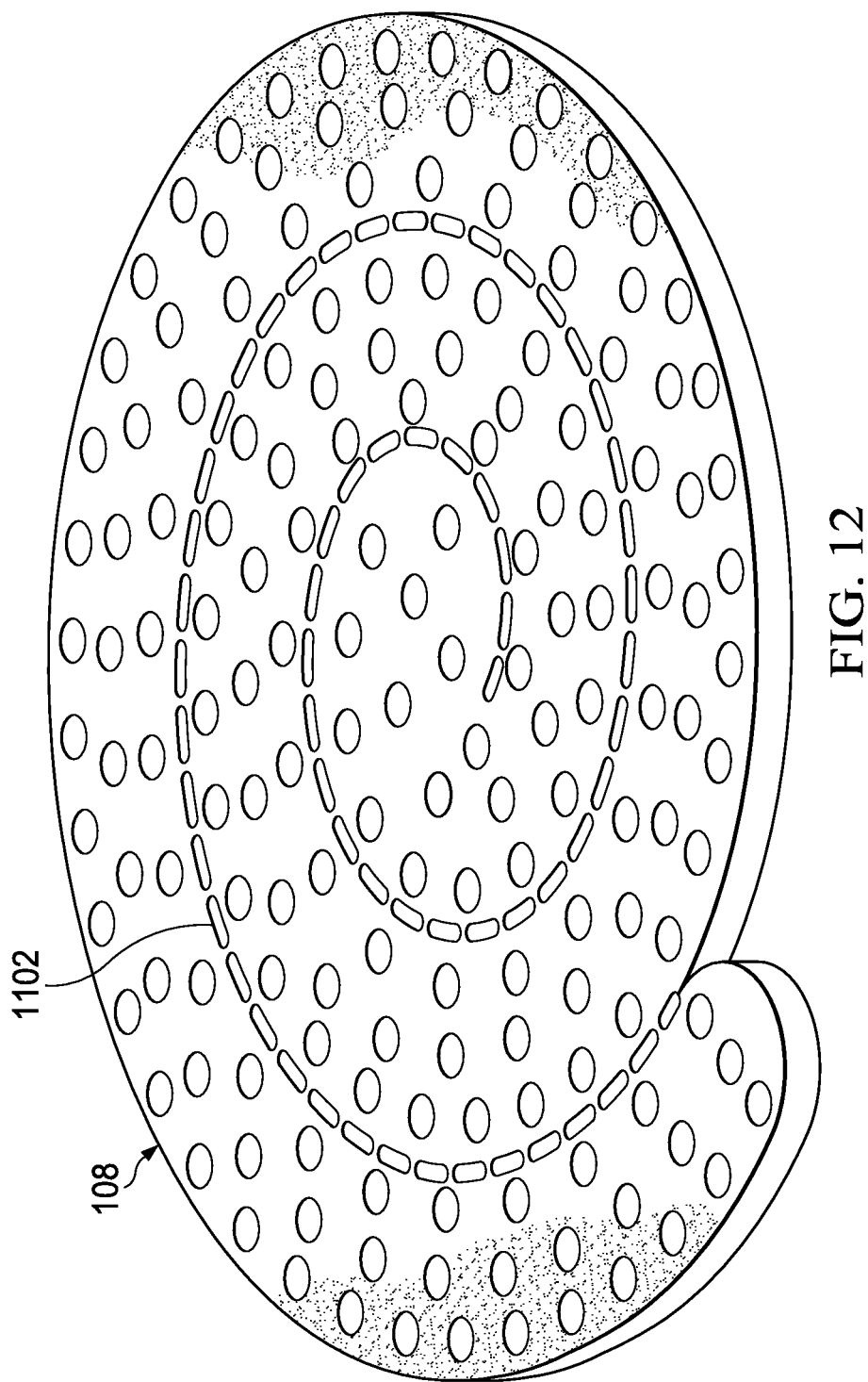
FIG. 12 is a simplified perspective view of the embodiment of FIG. 11.

For example, in the embodiment of FIG. 11 the contact layer 108 is spirally-shaped and includes perforations 1102 disposed within the contact layer 108 in a spiral. FIG. 12 illustrates a perspective view of the contact layer 108 of FIG. 11. The contact layer 108 may be separated along some portion of the perforations 1102 to yield a spiral having a desired size.

Figure 13:
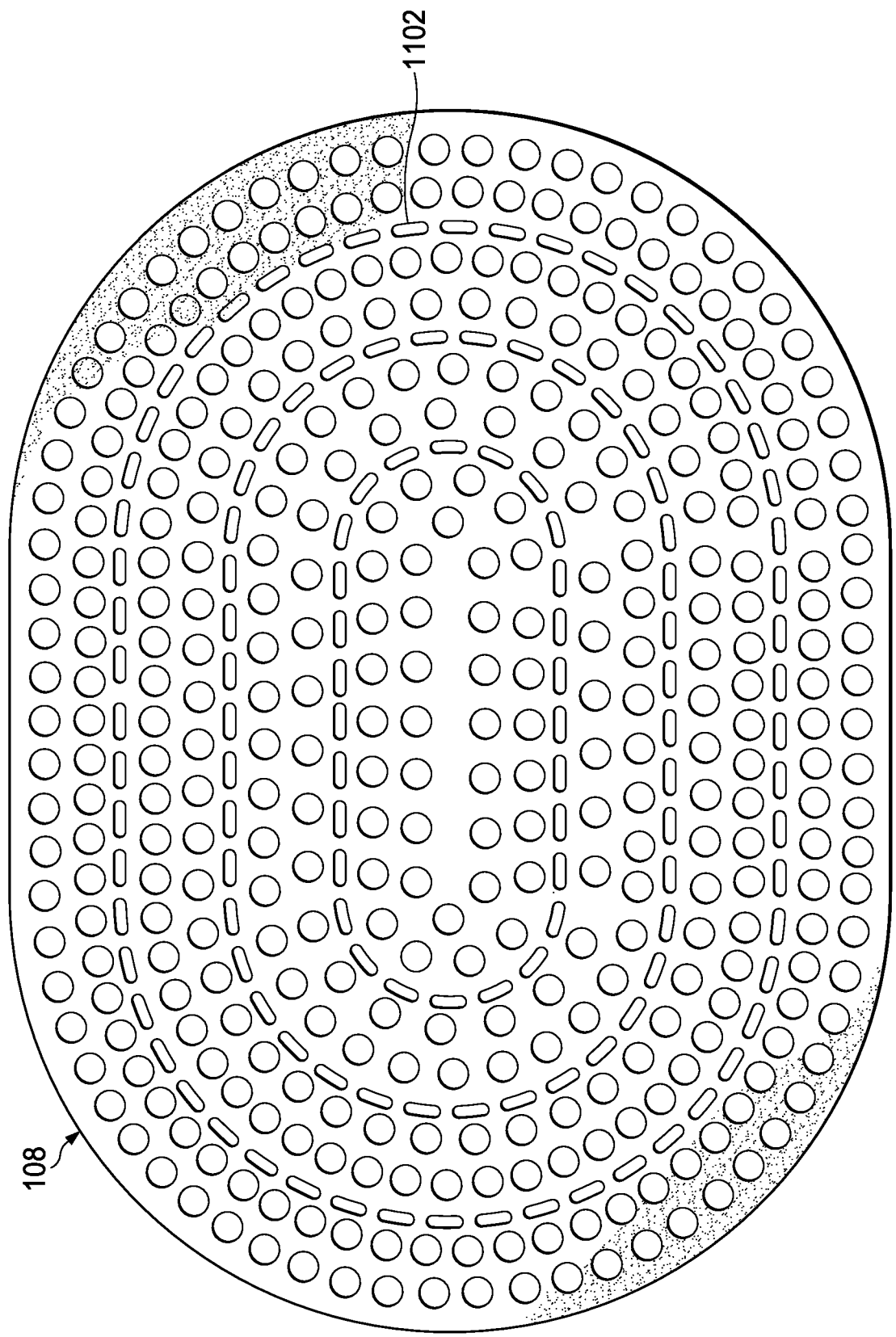
FIG. 13 is a simplified planar view of another example embodiment of a contact layer that may be associated with the therapy system of FIG. 1.
Figure 14:
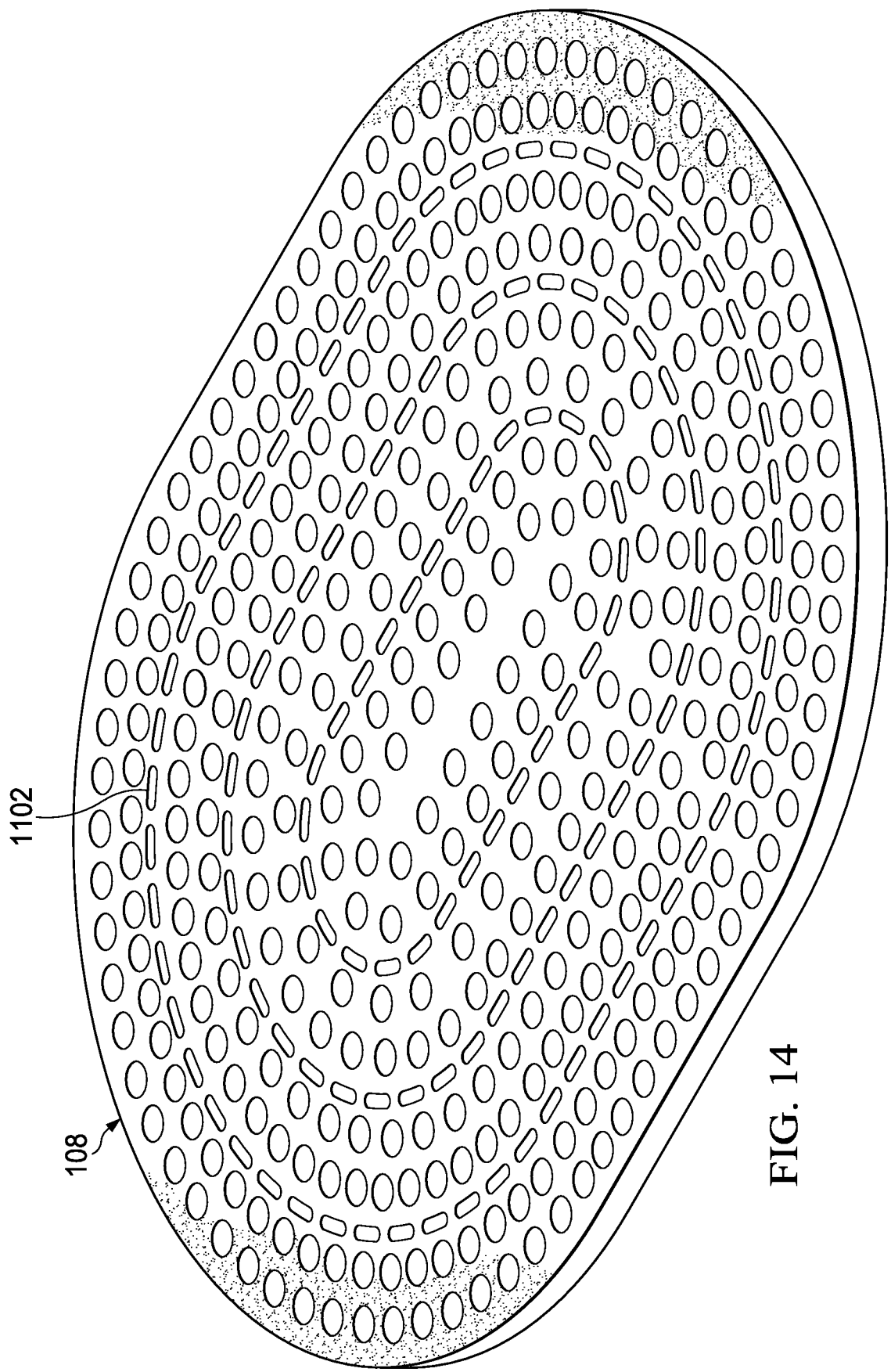
FIG. 14 is a simplified perspective view of the embodiment of FIG. 13.

In the embodiment of FIG. 13 the contact layer 108 is elliptically-shaped and includes perforations 1102 disposed within the contact layer 108 in a plurality of concentric ellipses. FIG. 14 illustrates a perspective view of the contact layer 108 of FIG. 13. The contact layer 108 may be separated along the perforations 1102 of one of the ellipses to yield an ellipse of a desired size.

Figure 15:
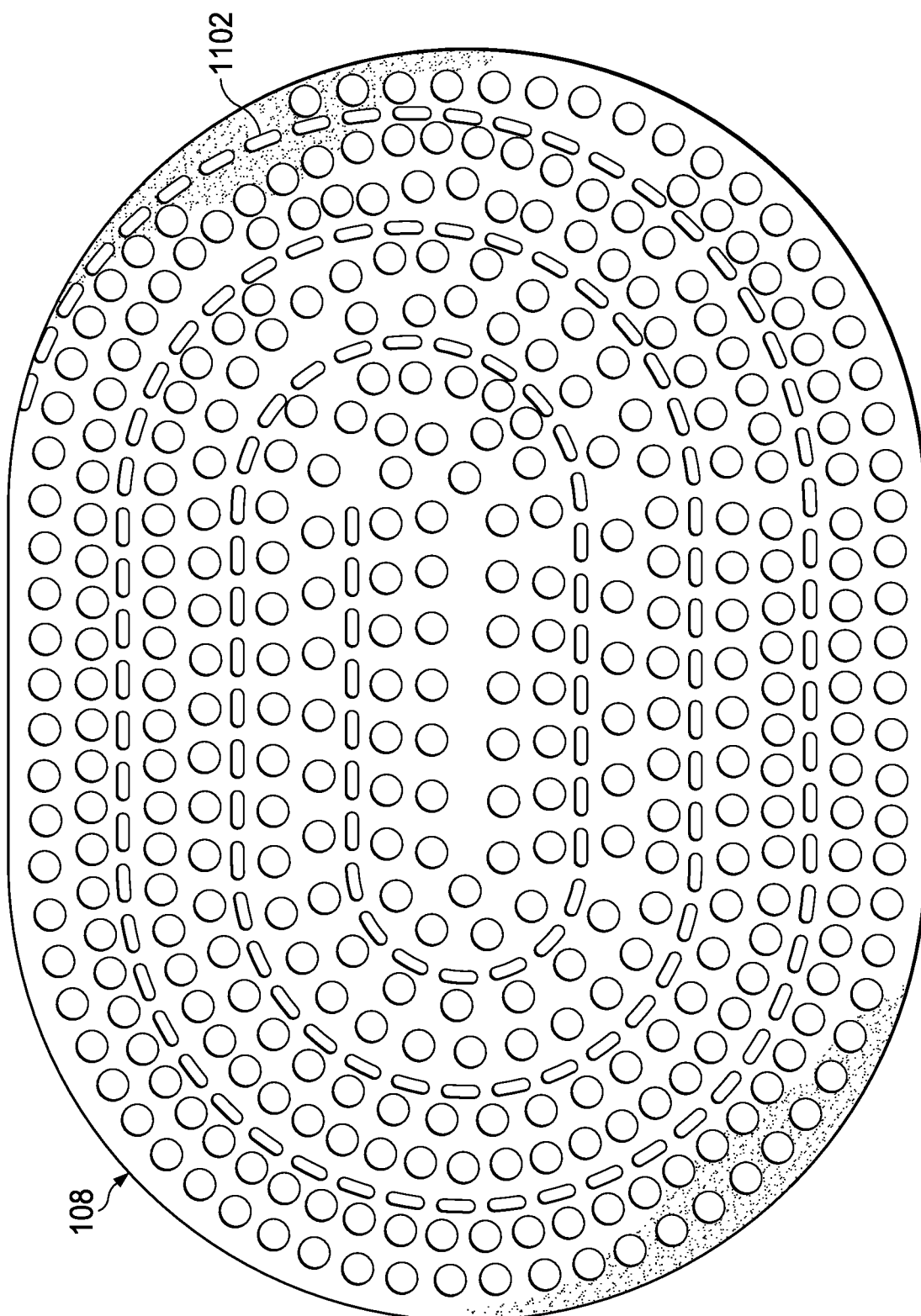
FIG. 15 is a simplified planar view of another example embodiment of a contact layer that may be associated with the therapy system of FIG. 1.
Figure 16:
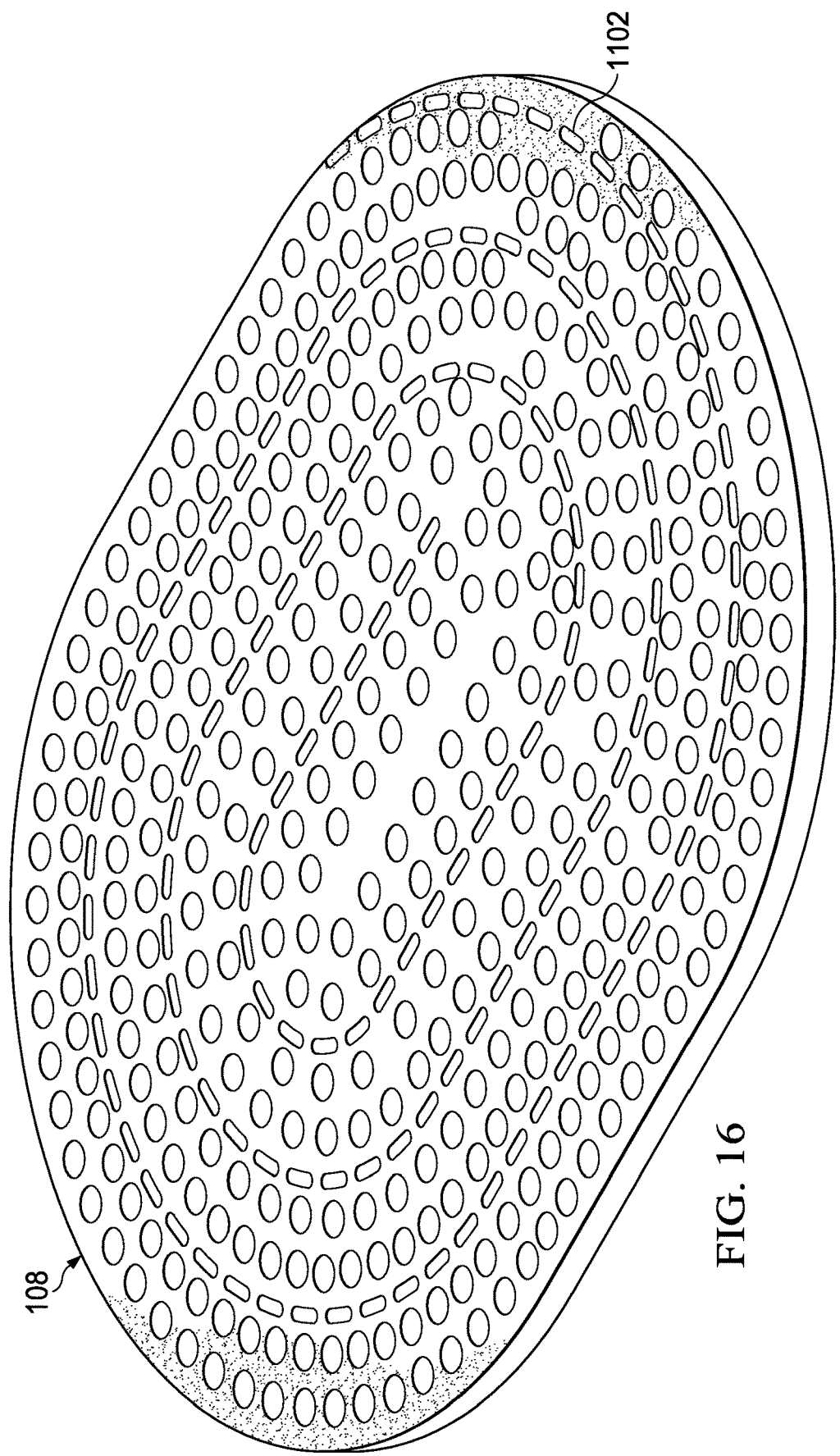
FIG. 16 is a simplified perspective view of the embodiment of FIG. 15.

In the embodiment of FIG. 15 the contact layer 108 is elliptically-shaped and includes perforations 1102 disposed within the contact layer 108 in a spiral. FIG. 16 illustrates a perspective view of the contact layer 108 of FIG. 15. The contact layer 108 may be separated along some portion of the perforations 1102 to yield a spiral having a desired size.

Figure 17:
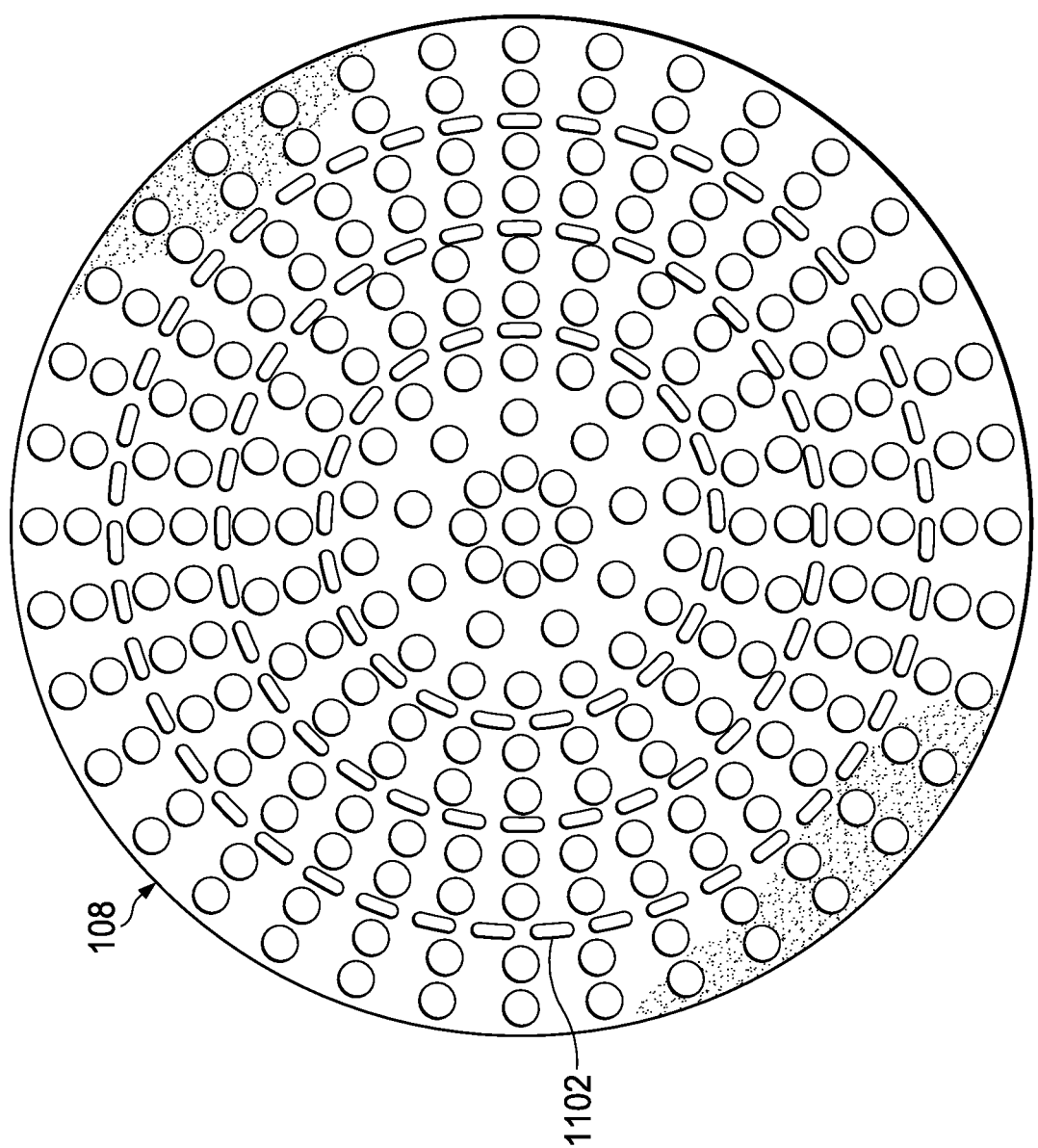
FIG. 17 is a simplified planar view of another example embodiment of a contact layer that may be associated with the therapy system of FIG. 1.
Figure 18:
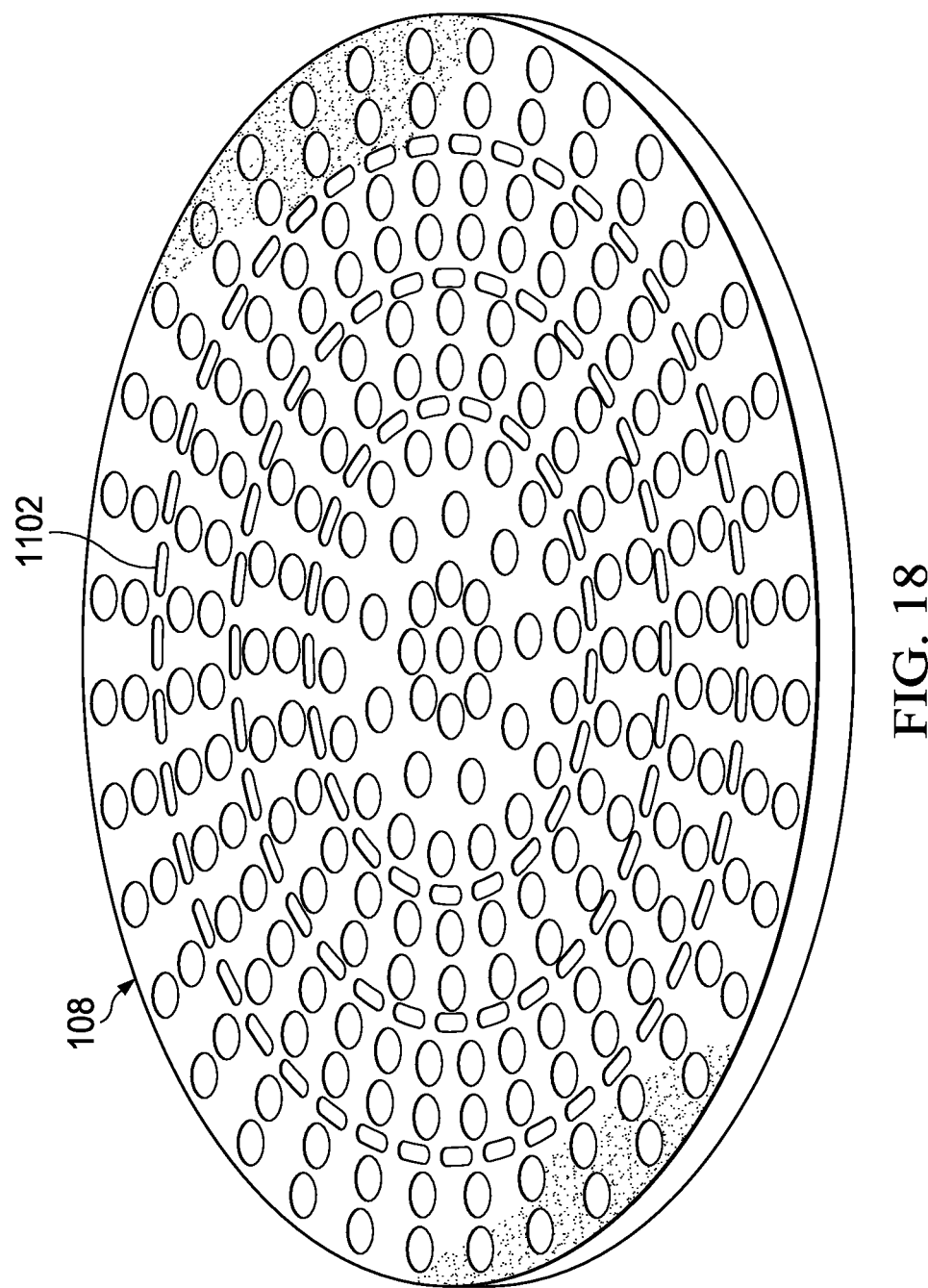
FIG. 18 is a simplified perspective view of the embodiment of FIG. 17.

In the embodiment of FIG. 17 the contact layer 108 is round and includes perforations 1102 disposed within the contact layer 108 in a plurality of concentric circles. FIG. 18 illustrates a perspective view of the contact layer 108 of FIG. 17. The contact layer 108 may be separated along the perforations 1102 of one of the circles to yield a circle of a desired size.

Figure 19:
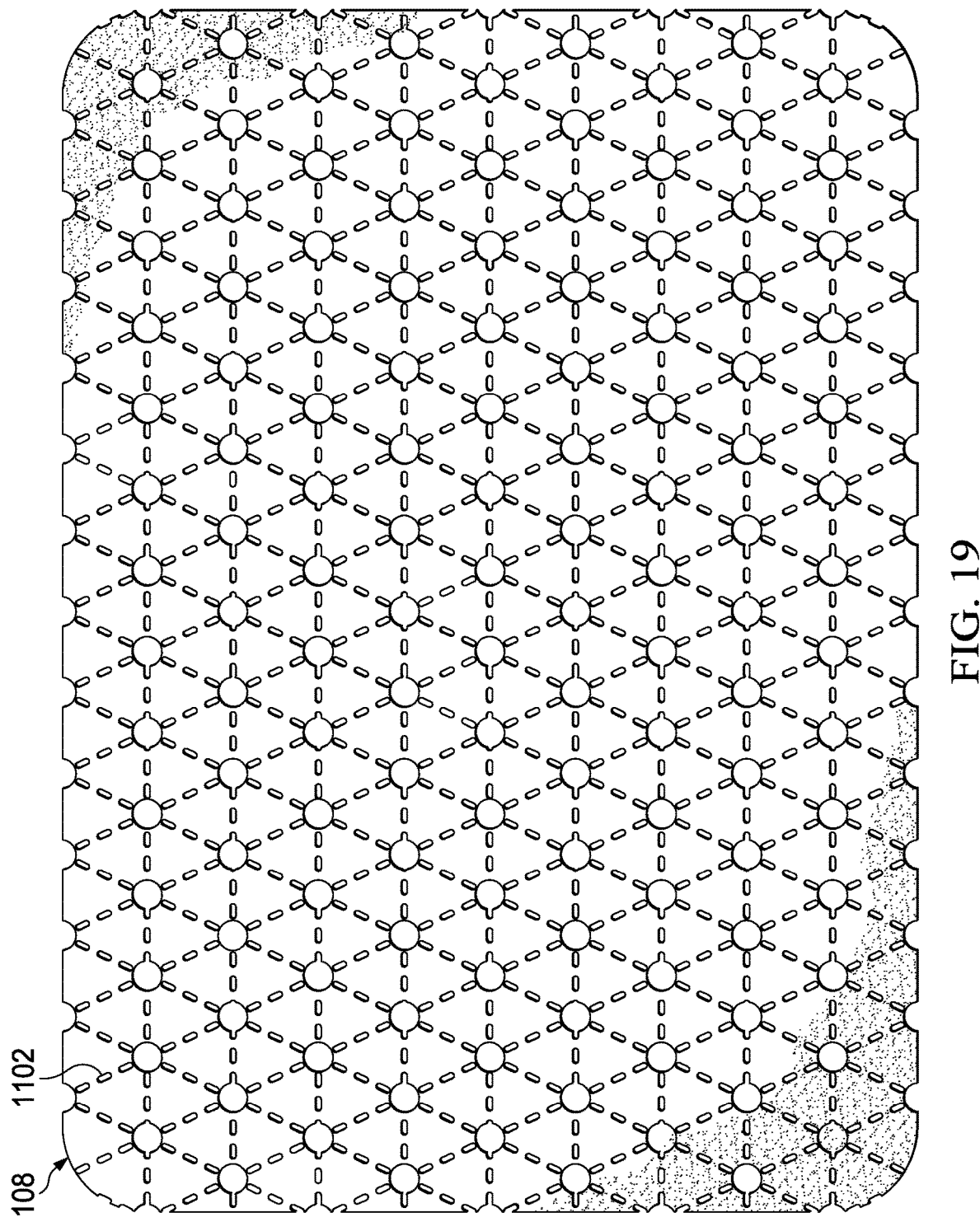
FIG. 19 is a simplified planar view of another example embodiment of a contact layer that may be associated with the therapy system of FIG. 1.
Figure 20:
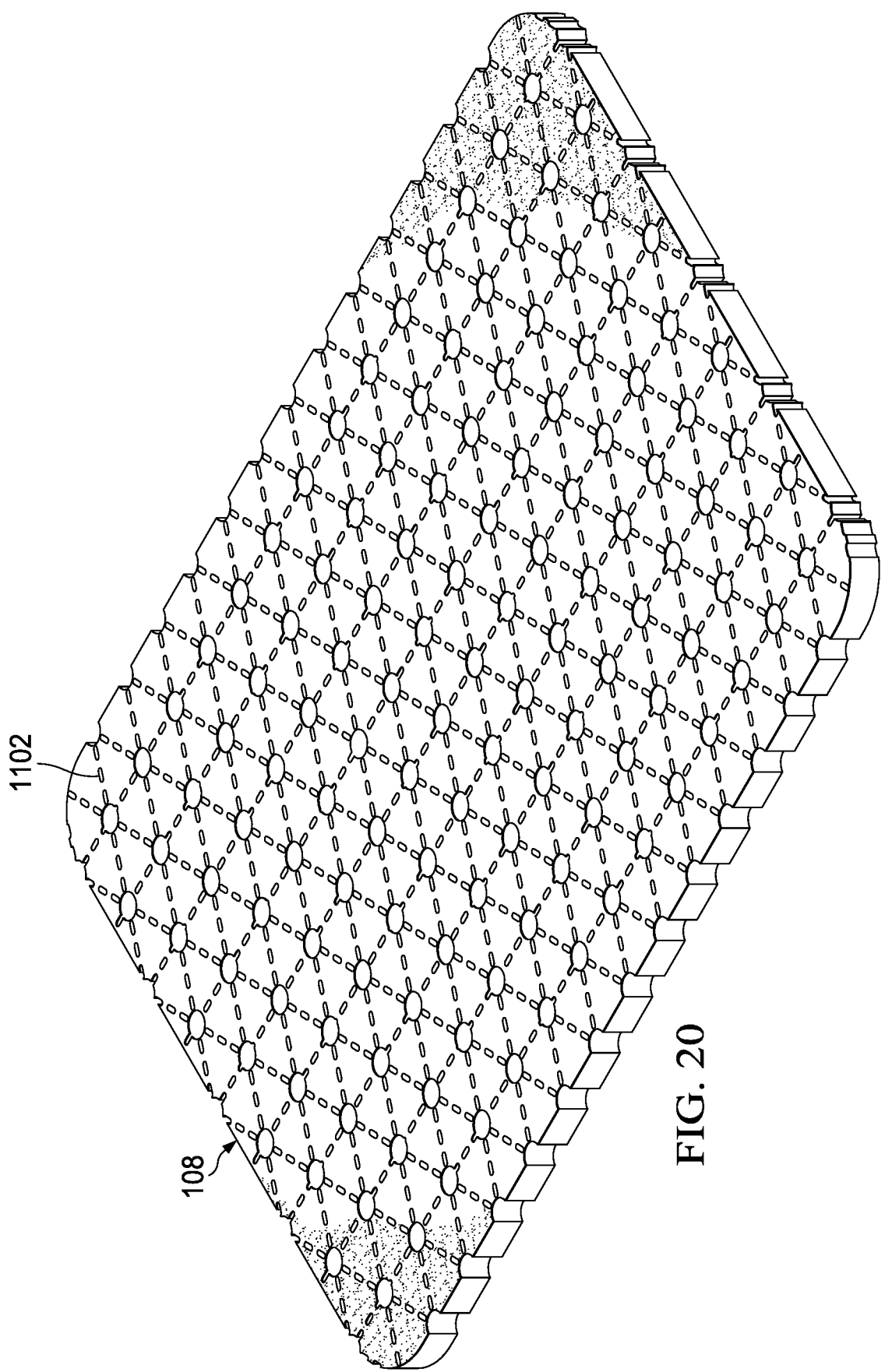
FIG. 20 is a simplified perspective view of the embodiment of FIG. 19.

In the embodiment of FIG. 19 the contact layer 108 is rectangular and includes perforations 1102 disposed within the contact layer 108 in a plurality of lines extending in multiple directions. FIG. 20 illustrates a perspective view of the contact layer 108 of FIG. 19. The contact layer 108 may be separated along the perforations 1102 of one or more of the lines to form a desired size and shape.

Figure 21:
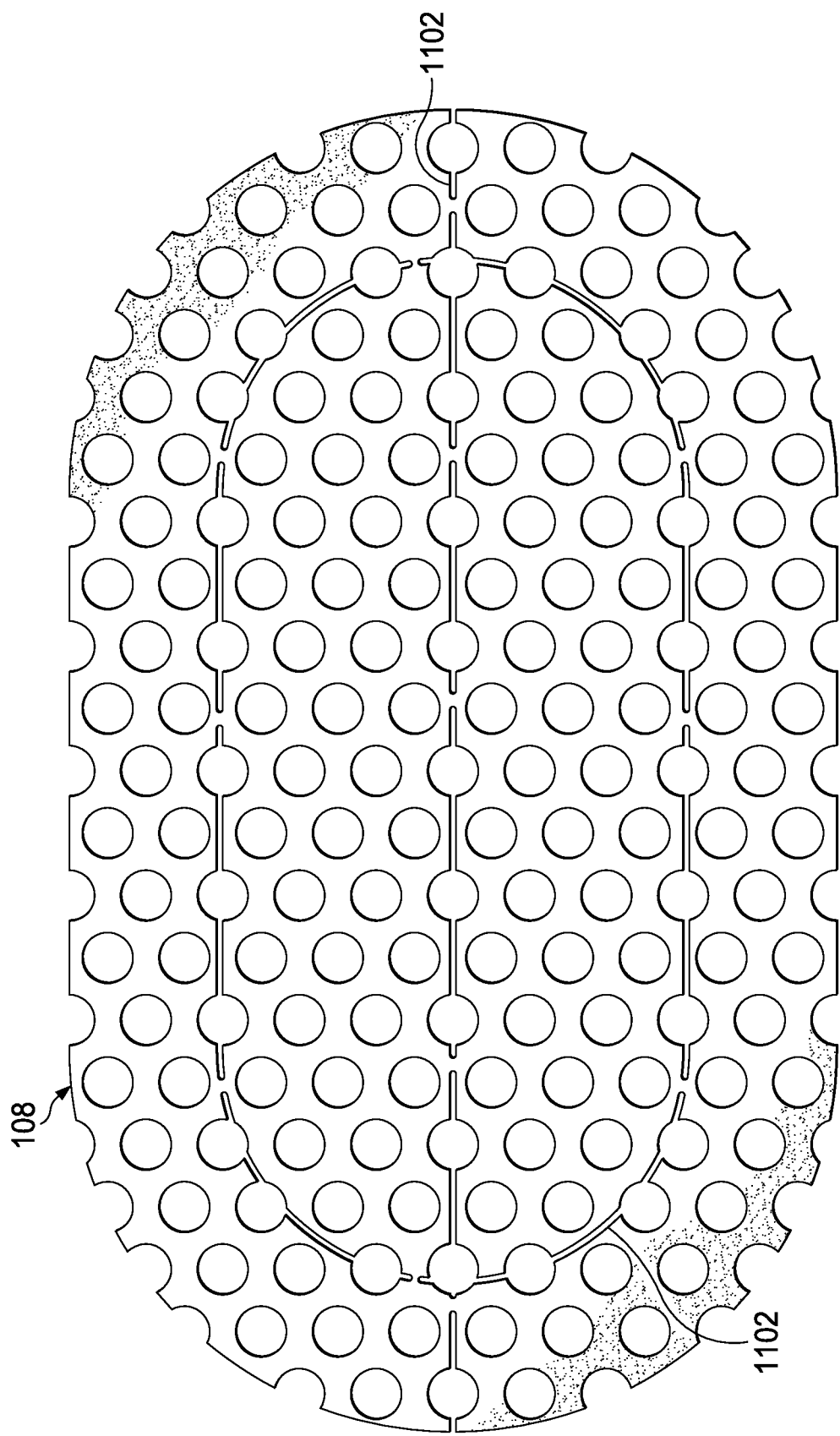
FIG. 21 is a simplified planar view of another example embodiment of a contact layer that may be associated with the therapy system of FIG. 1.
Figure 22:
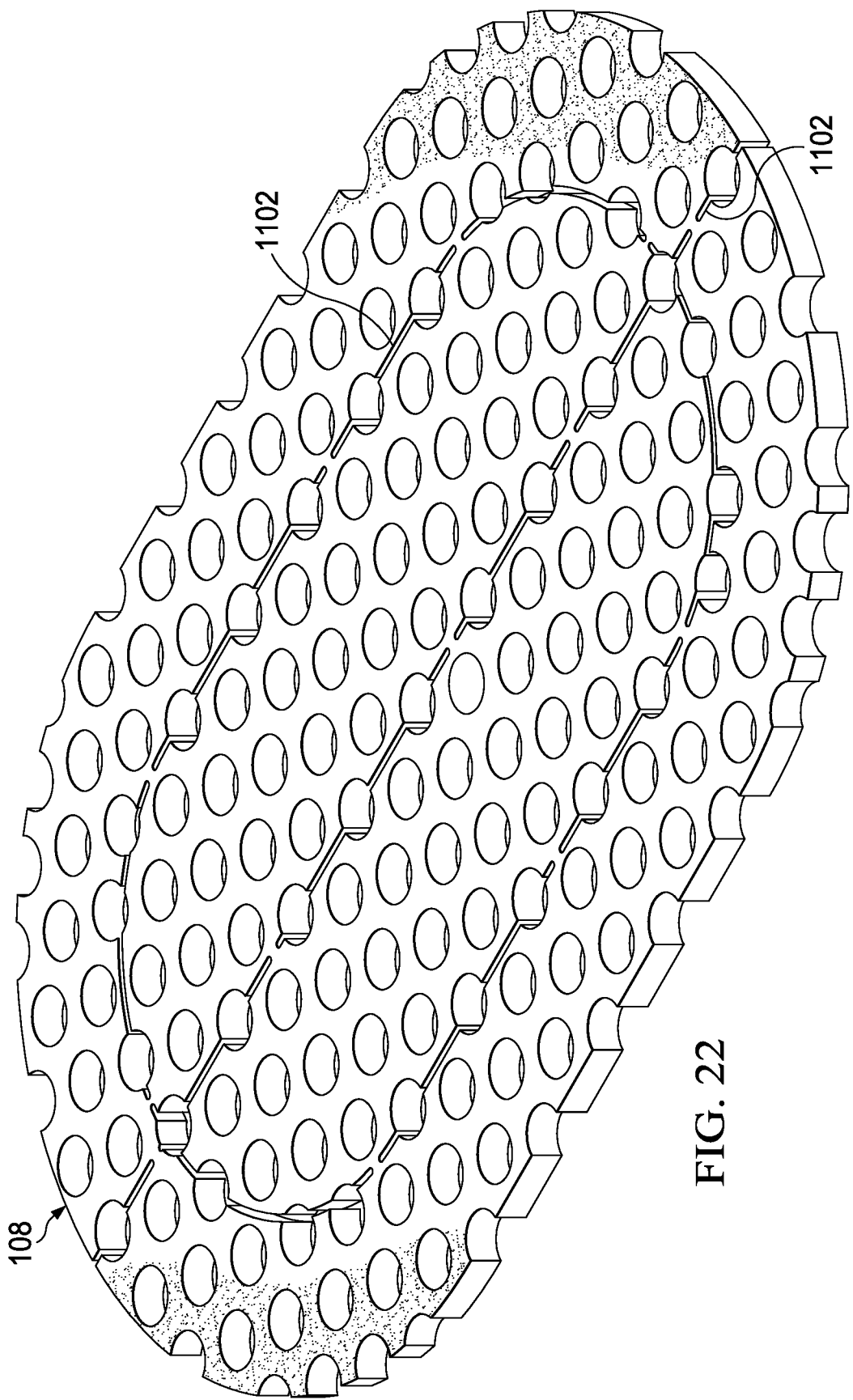
FIG. 22 is a simplified perspective view of the embodiment of FIG. 21.

In the embodiment of FIG. 21 the contact layer is an oval and includes perforations 1102 disposed within the contact layer 108 in an oval and in a line. FIG. 22 illustrates a perspective view of the contact layer 108 of FIG. 21. The contact layer 108 may be separated along the perforations 1102 of one or more of the lines to form a desired size and shape.

Figure 23:
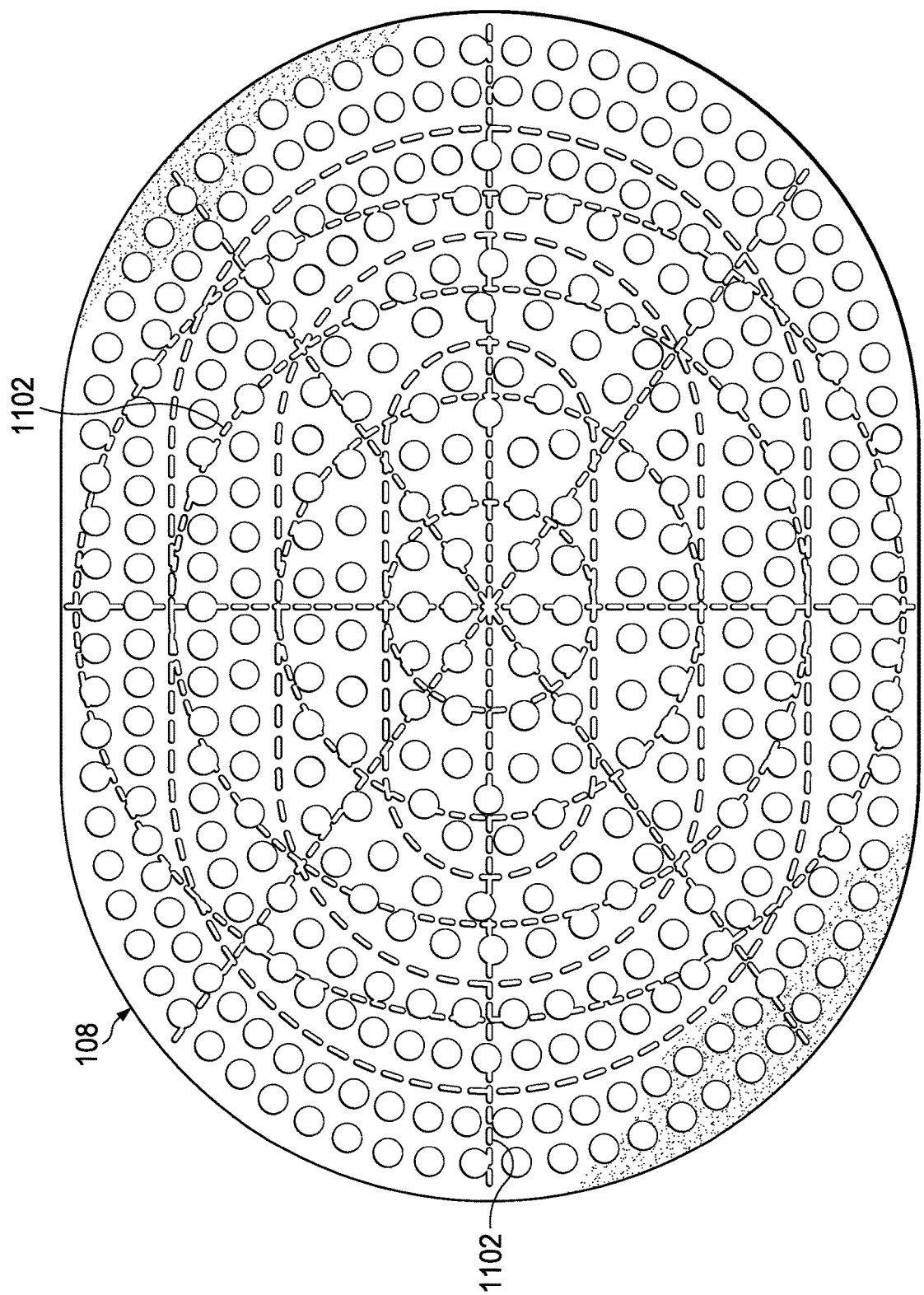
FIG. 23 is a simplified planar view of another example embodiment of a contact layer that may be associated with the therapy system of FIG. 1.
Figure 24:
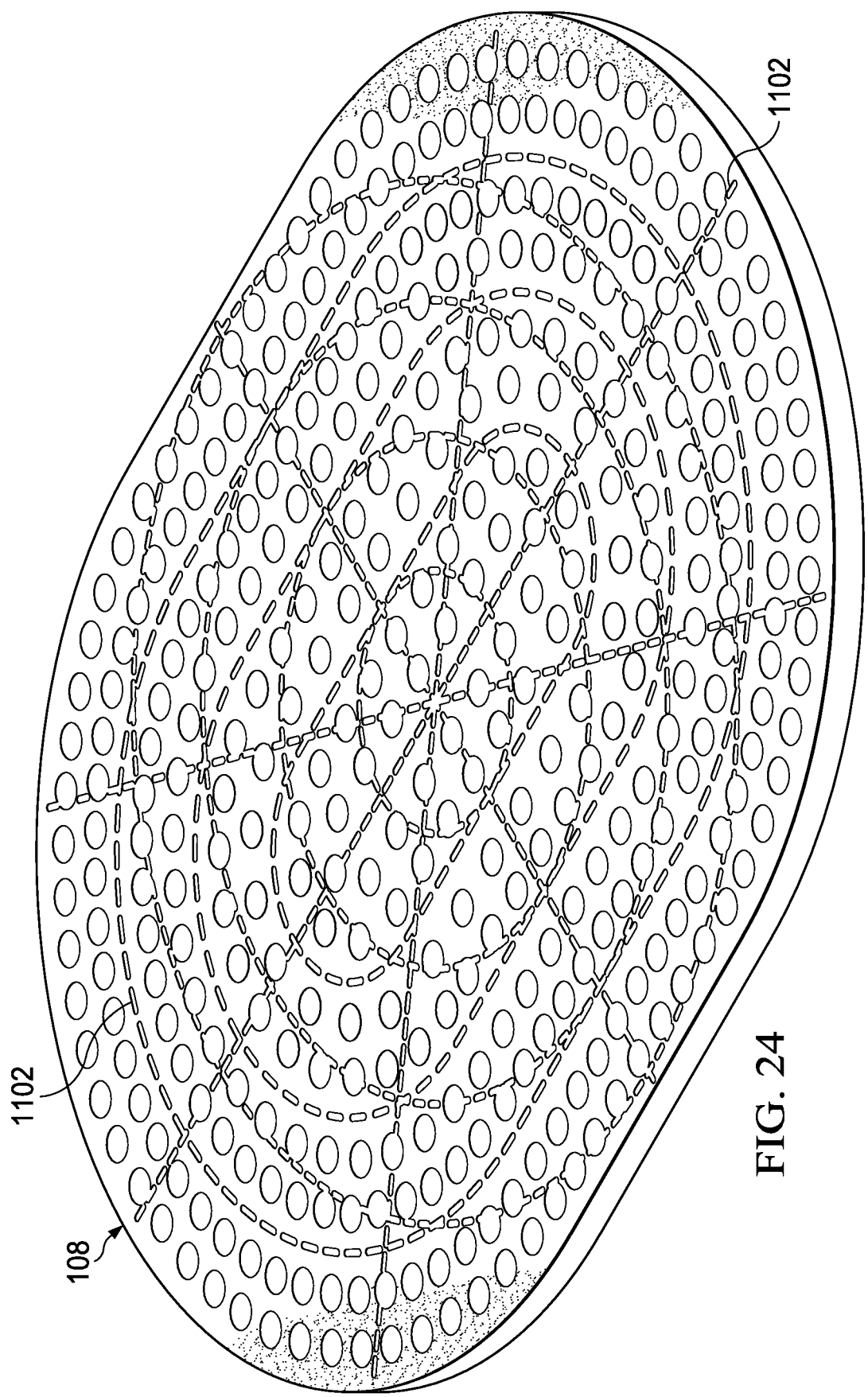
FIG. 24 is a simplified perspective view of the embodiment of FIG. 23.

In the embodiment of FIG. 23 the contact layer 108 is an oval and includes perforations 1102 disposed within the contact layer 108 in concentric circles and oval and in lines radiating from the center. FIG. 24 illustrates a perspective view of the contact layer 108 of FIG. 23. The contact layer 108 may be separated along the perforations 1102 of one or more of the lines to form a desired size and shape.

In some embodiments, the contact layer 108 may be provided as a part of a kit. In various embodiments, for example, the kit may include a contact layer 108, a secondary layer, a cover, or combinations thereof. Generally, a secondary layer may comprise fluid pathways interconnected so as to improve distribution or collection of fluids. For example, in some embodiments, a secondary layer may comprise or consist essentially of a porous material. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. In some examples, a secondary layer may comprise or consist essentially of reticulated polyurethane foam.

In some embodiments, the kit may include two or more contact layers 108, two or more secondary layers, or combinations thereof. The two or more contact layer 108 may vary with respect to various parameters such as thickness; density; presence, size, number, and/or distribution of apertures; or the like. For example, the kit may include a contact layer 108 having a particular property such as thickness, density, or apertures and another contact layer 108 having another property. Similarly, the two or more secondary layers may vary with respect to various properties, such as thickness, density, or porosity.

Figure 25:
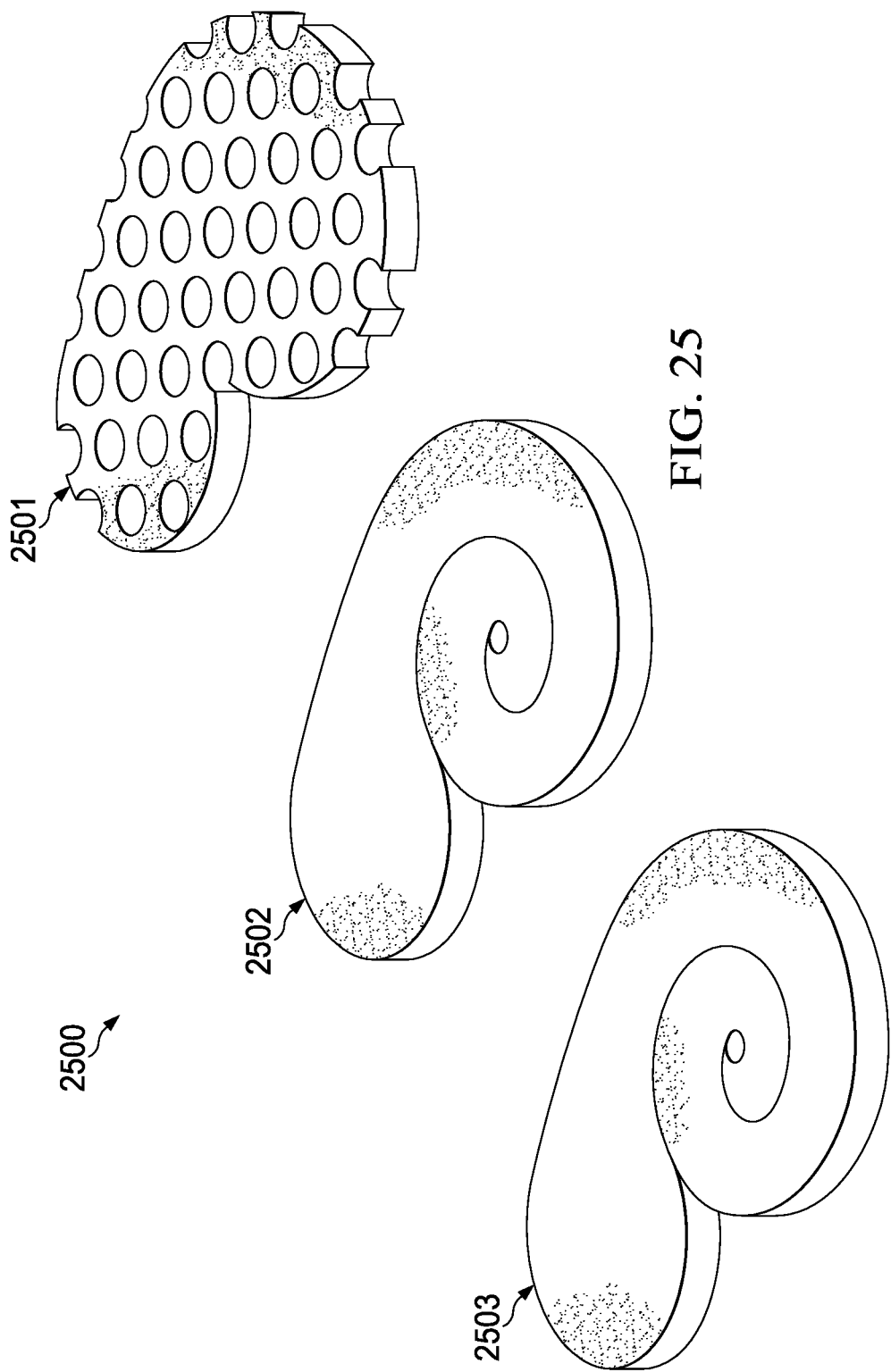
FIG. 25 is a simplified perspective view of a kit including a contact layer.

For example, FIG. 25 illustrates an embodiment of a kit 2500 including a first contact layer 2501, a second contact layer 2502, and a secondary layer 2503. The first contact layer 2501 may include apertures while apertures may be absent from the second contact layer 2502. The first contact layer 2501 and the second contact layer 2502 may each include perforations, enabling the first contact layer 2501 and the second contact layer 2502 to be conformed to a portion of a tissue site. For example, in some embodiments the first contact layer 2501 may be conformed to a first portion of a tissue site and the second contact layer 2502 may be conformed to a second portion of a tissue site, depending upon the desired therapy of the tissue site.

Figure 26:
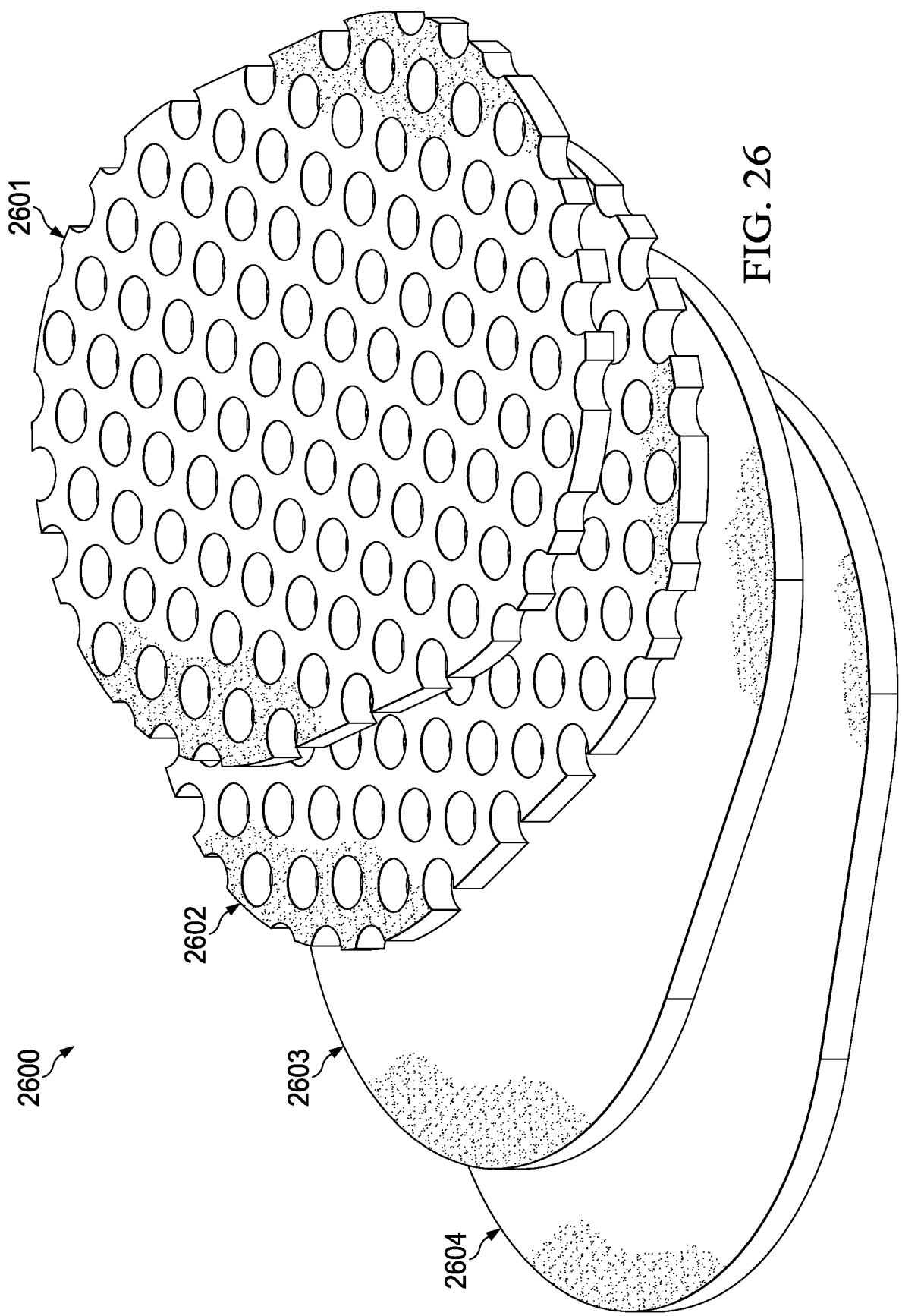
FIG. 26 is another simplified perspective view of a kit including a contact layer.

FIG. 26 illustrates an embodiment of a kit 2600 including a first contact layer 2601, a second contact layer 2602, and a first secondary layer 2603, and a second secondary layer 2604. The first contact layer 2601 and the second contact layer 2602 may vary as to thickness and the first secondary layer 2603 and the second secondary layer 2604 may also vary as to thickness. In various embodiments, the first secondary layer 2603 and the second secondary layer 2604 may be used separately or together to yield a desired thickness. Similarly, the first contact layer 2601 and the second contact layer 2602 may be used separately or together to yield a desired thickness, according to the needs of a particularly therapy.

Methods of Use

In operation, a contact layer may be employed in treating a tissue site, for example, tissue having debris that may be desirably disrupted. For example, the tissue site may include biofilms, necrotic tissue, lacerated tissue, devitalized tissue, contaminated tissue, damaged tissue, infected tissue, exudate, highly viscous exudate, fibrinous slough, and/or other material that can generally be referred to as debris. Such debris may inhibit the efficacy of tissue treatment and slow the healing of the tissue site.

As an example, during treatment of a tissue site, a biofilm may develop on or in the tissue site. Biofilms may include a microbial infection that can cover a tissue site and impair healing of the tissue site. Biofilms can also lower the effectiveness of topical antibacterial treatments by preventing the topical treatments from reaching the tissue site. The presence of biofilms can increase healing times, reduce the efficacy and efficiency of various treatments, and increase the risk of a more serious infection. Additionally or alternatively, some tissue sites may not heal according to the normal medical protocol and may develop areas of necrotic tissue. Necrotic tissue may include dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax. Conventionally, eschar may be generally difficult to move without the use of surgical cutting instruments.

In various embodiments, the debris may cover all or a portion of the tissue site. If the debris is at or in in the tissue site, the tissue site may be treated with various processes to disrupt the debris. Examples of disruption can include softening of the debris, separation of the debris from desired tissue, such as the subcutaneous tissue, preparation of the debris for removal from the tissue site, and removal of the debris from the tissue site.

In some embodiments, the diameter of the orifices may be selected to permit flow of debris through the orifices and associated apertures. For example, in some embodiments the diameter of the orifices may be selected based on the size of the debris to be lifted from the tissue site. Generally, larger orifices may allow larger debris to pass through the contact layer and smaller orifices may allow smaller debris to pass through the contact layer while blocking debris larger than the orifices. In some embodiments, successive applications of a contact layer can progressively smaller diameters of the orifices. Sequentially decreasing diameters of the orifices may also aid in fine-tuning a level of tissue disruption to the debris during the treatment of the tissue site. The diameter of the orifices can also influence fluid movement in the contact layer.

The contact layer may be prepared for use by selecting a desired orifice size from either the apertures of the first diameter range or the second diameter range and configuring the contact layer such that orifices of the desired orifice size may be contacted with the tissue site. In some embodiments, such as the in the embodiments of FIGS. 2, 3, 4, and 5, configuring the contact layer may include orienting the contact layer such that the orifices of a desired size may be disposed adjacent to the tissue site. For example, a user may orient the contact layer such that the orifices having a diameter in a first range are in contact with the tissue or such that the orifices having a diameter in a second range are in contact with the tissue site.

Additionally or alternatively, in some embodiments such as the embodiment of FIGS. 6 and 7, configuring the contact layer may include determining whether to remove the removable portions of the contact or to leave the removable portions fitted within the contact layer. For example, if the user desires to use the orifices having a diameter in the first range, the user may leave the removable portions within the contact layer or, if the user desires to use the orifices having a diameter in the second range, the user may remove the removable portions from the contact layer.

Additionally or alternatively, in some embodiments such as the embodiment of FIG. 8, configuring the contact layer may include placing the contact layer in a conformation in which the orifices of a desired size may be placed in contact with the tissue site. With the contact layer configured for placement, the contact layer may be placed within, over, on, or otherwise proximate to a tissue site.

Additionally or alternatively, in some embodiments configuring the contact layer may include separating a portion of contact layer, such as along a perforation, to form a desired size or shape. In some embodiments, a portion of a first contact layer may be placed over a first portion of a tissue site and a portion of a second contact layer may be placed over a second portion of the tissue site. For example, utilizing portions from difference contact layers to cover different portions of a tissue site may be effective to disrupt debris at a first portion of the tissue site while the second portion of the tissue site remains relatively undisrupted.

In some embodiments, a cover may be placed over the contact layer and sealed to an attachment surface near the tissue site. For example, the cover may be sealed to undamaged epidermis peripheral to a tissue site. Thus, the dressing can provide a sealed therapeutic environment proximate to a tissue site, substantially isolated from the external environment, and the negative-pressure source can reduce the pressure in the sealed therapeutic environment. Negative pressure applied across the tissue site through the contact layer in the sealed therapeutic environment can induce macrostrain and microstrain in the tissue site, as well as remove exudates and other fluids from the tissue site, which can be collected in container.

In some embodiments, such as where the contact layer is employed to disrupt debris at a tissue site, the application of negative pressure to the tissue site via the contact layer can generate concentrated stresses in the debris adjacent and/or proximate to the apertures in the contact layer. The concentrated stresses can cause macro-deformations of the debris and the subcutaneous tissue, for example, which may draw portions of the debris and the subcutaneous tissue into the apertures. Similarly, the apertures of the contact layer may create macro-pressure points in portions of the debris and the subcutaneous tissue that are in contact with a tissue-facing surface of the contact layer, causing tissue puckering and nodules to be formed in the debris and the subcutaneous tissue. In some embodiments, formation of the nodules may lift debris and particulates off of the surrounding tissue, for example, operating in a piston-like manner to move debris toward and into the contact layer.

Advantages

In various embodiments, a therapy system or components thereof, such as the contact layer, may be advantageously employed in the provision of therapy, such as negative pressure therapy, to a patient. For example, a contact layer configurable such that at least a portion of the apertures include a first plurality of orifices having a diameter in a first diameter range and such that at least a portion of the apertures include a second plurality of orifices having a diameter in a second diameter range may allow a user to choose an aperture size effective for obtaining desired results, such as the disruption of debris at the tissue site, in the context of the therapy. Thus, a single contact layer may be employed more effectively and efficiently across a wider variety of therapies.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the container 112 may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for treating a tissue site, the apparatus comprising:
   a contact layer formed from a compressible material, the contact layer comprising a plurality of apertures defined by walls extending at least partially through the contact layer;
   at least a portion of the apertures including a first plurality of orifices having a diameter in a first diameter range;
   at least a portion of the apertures including a second plurality of orifices having a diameter in a second diameter range; and
   a cover configured to form a sealed space including the contact layer and the tissue site;
   wherein the contact layer has a first thickness at ambient pressure, wherein the contact layer is configured to compress to a second thickness in response to a reduced pressure applied to the sealed space, wherein the first plurality of orifices and the second plurality of orifices are configured to receive tissue to form nodules at the tissue site in response to the reduced pressure applied to the sealed space, wherein the nodules have a height no greater than the second thickness.

2. The apparatus of claim 1, wherein the first diameter range is from about 2 mm to about 6 mm.

3. The apparatus of claim 1, wherein the second diameter range is from about 8 mm to about 15 mm.

4. The apparatus of claim 1, wherein the first plurality of orifices are grouped together and the second plurality of orifices are grouped together.

5. The apparatus of claim 1, wherein the contact layer comprises a first surface that is substantially planar, and the first plurality of orifices are in the first surface.

6. The apparatus of claim 5, wherein the contact layer comprises a second surface that is substantially planar, and the second plurality of orifices is in the second surface.

7. The apparatus of claim 1, wherein each of the plurality of apertures includes an orifice in the first diameter range and an orifice in the second diameter range.

8. The apparatus of claim 7, wherein the plurality of apertures are conical.

9. The apparatus of claim 1, wherein each of the apertures has a substantially constant diameter.

10. The apparatus of claim 1, wherein the apertures of the first portion of the plurality of apertures are disposed in a first segment of the contact layer and the apertures of the second portion of the plurality of apertures are disposed in a second segment of the contact layer.

11. The apparatus of claim 1, wherein the contact layer comprises a first sublayer and a second sublayer joined to the first sublayer, the first sublayer and the second sublayer formed from the compressible material.

12. The apparatus of claim 11, wherein the first sublayer comprises a first portion of the plurality of apertures having orifices in the first diameter range and second sublayer comprises a second portion of the plurality of apertures having orifices in the second diameter range.

13. The apparatus of claim 12, wherein the apertures of the first sublayer are aligned with the apertures of the second sublayer.

14. The apparatus of claim 12, wherein the apertures of the first sublayer are offset from the apertures of the second sublayer.

15. The apparatus of claim 1, wherein the compressible material comprises a thermoplastic elastomer.

16. The apparatus of claim 1, wherein the compressible material comprises a thermoplastic polyurethane.

17. The apparatus of claim 1, further comprising a reduced-pressure source adapted to apply a reduced pressure to the sealed space.

18. The apparatus of claim 1, wherein the apparatus is configured to be positioned adjacent to the tissue site and, when the apparatus is positioned adjacent to the tissue site, at least one of the first plurality of orifices and the second plurality of orifices is in contact with the tissue site.

19. The apparatus of claim 1, wherein the contact layer is separable along a separation-line.

20. The apparatus of claim 19, wherein the separation-line includes perforations.

21. The apparatus of claim 19, wherein the separation-line is in the shape of a line, a circle, an ellipse, an oval, or combinations thereof.

22. A method for treating a tissue site, the method comprising:
    providing a contact layer formed from a compressible material and comprising walls defining a plurality of apertures extending at least partially through the contact layer, the contact layer being configurable such that at least a portion of the apertures include a first plurality of orifices having a diameter in a first diameter range and at least a portion of the apertures include a second plurality of orifices having a diameter in a second diameter range, the contact layer having a first thickness at ambient pressure;
    selecting a desired orifice size from either the apertures of the first diameter range or the second diameter range;
    configuring the contact layer such that orifices of the desired orifice size are in contact with the tissue site;
    sealing a sealing member to tissue surrounding the tissue site to form a sealed space enclosing the contact layer;
    fluidly coupling a negative-pressure source to the sealed space; and
    supplying reduced pressure to the sealed space and the contact layer to compress the contact layer to a second thickness that is less than the first thickness and to draw tissue through the orifices of the desired orifice size and into the apertures to form nodules, the nodules having a height no greater than the second thickness.

23. The method of claim 22, wherein the first diameter range is from about 2 mm to about 6 mm.

24. The method of claim 22, wherein the second diameter range is from about 8 mm to about 15 mm.

25. The method of claim 22, wherein first plurality of orifices are grouped together and the second plurality of orifices are grouped together.

26. The method of claim 22, wherein the contact layer comprises a first substantially planar surface comprising the first plurality of orifices.

27. The method of claim 26, wherein the contact layer comprises a second substantially planar surface comprising the second plurality of orifices.

28. The method of claim 22, wherein each of the plurality of apertures includes an orifice in the first diameter range and an orifice in the second diameter range.

29. The method of claim 28, wherein the plurality of apertures are conical.

30. The method of claim 22, wherein a first portion of the plurality of apertures includes orifices in the first diameter range and a second portion of the plurality of apertures includes orifices in the second diameter range.

31. The method of claim 30, wherein each of the apertures has a substantially constant diameter.

32. The method of claim 30, wherein the apertures of the first portion of the plurality of apertures are disposed in a first segment of the contact layer and the apertures of the second portion of the plurality of apertures are disposed in a second segment of the contact layer.

33. The method of claim 22, wherein the contact layer comprises a first sublayer and a second sublayer joined to the first sublayer, the first sublayer and the second sublayer formed from the compressible material.

34. The method of claim 33, wherein the first sublayer comprises a first portion of the plurality of apertures having orifices in the first diameter range and second sublayer comprises a second portion of the plurality of apertures having orifices in the second diameter range.

35. The method of claim 34, wherein the apertures of the first sublayer are aligned with the apertures of the second sublayer.

36. The method of claim 34, wherein the apertures of the first sublayer are offset from the apertures of the second sublayer.

37. The method of claim 22, wherein the contact layer further comprises a plurality of removable portions, each of the plurality of removable portions having at least one of the apertures including orifices in the first diameter range and being removable from the contact layer to form at least one of the apertures including orifices in the second diameter range.

38. The method of claim 22, wherein the compressible material comprises a thermoplastic elastomer.

39. The method of claim 22, wherein the compressible material comprises a thermoplastic polyurethane.

40. The method of claim 22, wherein the contact layer is separable along a separation-line.

41. The method of claim 40, wherein the separation-line includes perforations.

42. The method of claim 40, wherein the separation-line is in the shape of a line, a circle, an ellipse, an oval, or combinations thereof.

43. The method of claim 40, wherein configuring the contact layer such that orifices of the desired orifice size are in contact with the tissue site includes separating a portion of the contact layer along the separation-line.

44. An apparatus for treating a tissue site, the apparatus comprising:
- a contact layer formed from a compressible material;
- a first plurality of apertures extending at least partially through the contact layer, the first plurality of apertures having a first plurality of orifices having a diameter in a first diameter range;
- a second plurality of apertures extending at least partially through the contact layer, the second plurality of apertures having a second plurality of orifices having a diameter in a second diameter range; and
- a cover configured to form a sealed space including the contact layer and the tissue site;
- wherein the first plurality of orifices and the second plurality of orifices are defined by walls in the contact layer, wherein the contact layer has a first thickness at ambient pressure, wherein the contact layer is configured to compress to a second thickness in response to a reduced pressure applied to the sealed space, wherein the first plurality of orifices and the second plurality of orifices are configured to receive tissue to form nodules at the tissue site in response to the reduced pressure applied to the sealed space, wherein the nodules have a height no greater than the second thickness.

45. The apparatus of claim 44, wherein the first diameter range is from about 2 mm to about 6 mm.

46. The apparatus of claim 44, wherein the second diameter range is from about 8 mm to about 15 mm.

47. The apparatus of claim 44, wherein the first plurality of orifices are grouped together and the second plurality of orifices are grouped together.

48. The apparatus of claim 44, wherein the contact layer comprises a first substantially planar surface comprising the first plurality of orifices.

49. The apparatus of claim 48, wherein the contact layer comprises a second substantially planar surface comprising the second plurality of orifices.

50. The apparatus of claim 44, wherein each of the first plurality of apertures and the second plurality of apertures includes an orifice in the first diameter range and an orifice in the second diameter range.

51. The apparatus of claim 50, wherein the first plurality of apertures and the second plurality of apertures are conical.

52. The apparatus of claim 44, wherein a first plurality of apertures includes orifices in the first diameter range and a second plurality of apertures includes orifices in the second diameter range.

53. The apparatus of claim 52, wherein each of the apertures has a substantially constant diameter.

54. The apparatus of claim 44, wherein the first plurality of apertures are disposed in a first segment of the contact layer and the second plurality of apertures are disposed in a second segment of the contact layer.

55. The apparatus of claim 44, wherein the contact layer comprises a first sublayer and a second sublayer joined to the first sublayer, the first sublayer and the second sublayer formed from the compressible material.

56. The apparatus of claim 55, wherein the first sublayer comprises the first plurality of apertures having orifices in the first diameter range and second sublayer comprises the second plurality of apertures having orifices in the second diameter range.

57. The apparatus of claim 56, wherein the apertures of the first sublayer are aligned with the apertures of the second sublayer.

58. The apparatus of claim 56, wherein the apertures of the first sublayer are offset from the apertures of the second sublayer.

59. The apparatus of claim 44, wherein the compressible material comprises a thermoplastic elastomer.

60. The apparatus of claim 44, wherein the compressible material comprises a thermoplastic polyurethane.

61. The apparatus of claim 44, further comprising a reduced-pressure source adapted to apply a reduced pressure to the sealed space.

62. The apparatus of claim 44, wherein the apparatus is configured to be positioned adjacent to the tissue site and, when the apparatus is positioned adjacent to the tissue site, at least one of the first plurality of orifices and the second plurality of orifices is in contact with the tissue site.

63. The apparatus of claim 44, wherein the contact layer is separable along a separation-line.

64. The apparatus of claim 63, wherein the separation-line includes perforations.

65. The apparatus of claim 63, wherein the separation-line is in the shape of a line, a circle, an ellipse, an oval, or combinations thereof.

66. An apparatus for treating a tissue site, the apparatus comprising:
- a contact layer formed from a compressible material, the contact layer comprising a plurality of removable portions, each of the plurality of removable portions having apertures including orifices in a first diameter range, wherein the removable portions are removable from the contact layer to form apertures including orifices in a second diameter range, the apertures defined by walls; and
- a cover configured to form a sealed space including the contact layer and the tissue site;
- wherein the contact layer has a first thickness at ambient pressure, wherein the contact layer is configured to compress to a second thickness in response to a reduced pressure applied to the sealed space, wherein the orifices in the first diameter range and the orifices in the second diameter range are configured to receive tissue to form nodules at the tissue site in response to pressure applied to the sealed space, wherein the nodules have a height no greater than the second thickness.

67. The apparatus of claim 66, wherein the first diameter range is from about 2 mm to about 6 mm.

68. The apparatus of claim 66, wherein the second diameter range is from about 8 mm to about 15 mm.

69. The apparatus of claim 66, wherein the compressible material comprises a thermoplastic elastomer.

70. The apparatus of claim 66, wherein the compressible material comprises a thermoplastic polyurethane.

71. The apparatus of claim 66, further comprising a reduced-pressure source adapted to apply a reduced pressure to the sealed space.

72. The apparatus of claim 66, wherein the apparatus is configured to be positioned adjacent to the tissue site and, when the apparatus is positioned adjacent to the tissue site, at least one of the orifices in the first diameter range and the orifices in the second diameter range is in contact with the tissue site.

73. A method for treating a tissue site, the method comprising:

providing a first contact layer formed from a compressible material and comprising walls defining a plurality of apertures extending at least partially through the contact layer, the first contact layer having a first thickness at ambient pressure;

providing a second contact layer formed from a compressible material;

configuring a portion of the first contact layer to cover a first portion of the tissue site;

configuring a portion of the second contact layer to cover a second portion of the tissue site;

positioning the portion of the first contact layer over the first portion of the tissue site;

positioning the portion of the second contact layer over the second portion of the tissue site;

sealing a sealing member to tissue surrounding the tissue site to form a sealed space enclosing the portion of the first contact layer and the portion of the second contact layer;

fluidly coupling a negative-pressure source to the sealed space; and supplying reduced pressure to the sealed space and the contact layer to draw tissue into the apertures to form nodules and to compress the first contact layer to a second thickness that is less than the first thickness, the nodules having a height no greater than the second thickness.

74. The method of claim 73, wherein configuring the first contact layer comprises separating the first contact layer along a first separation-line.

75. The method of claim 74, wherein the first separation-line includes perforations.

76. The method of claim 74, wherein the first separation-line is in the shape of a line, a circle, an ellipse, an oval, or combinations thereof.

77. The method of claim 73, wherein configuring the second contact layer comprises separating the second contact layer along a second separation-line.

78. The method of claim 77, wherein the second separation-line includes perforations.

79. The method of claim 77, wherein the second separation-line is in the shape of a line, a circle, an ellipse, an oval, or combinations thereof.

* * * * *